United States Patent [19]
Kissinger et al.

[11] Patent Number: 6,062,224
[45] Date of Patent: May 16, 2000

[54] MOVEMENT-RESPONSE SYSTEM FOR CONDUCTING TESTS ON FREELY-MOVING ANIMALS

[75] Inventors: Candice B. Kissinger; Curtis E. Bohs, both of West Lafayette; Donnie A. Evans, Dayton; William J. Schmidt, West Lafayette; Scott R. Peters, West Lafayette; W. Gamini Gunaratna, West Lafayette; James M. Hampsch, Lafayette, all of Ind.

[73] Assignee: Bioanalytical Systems, Inc., West Lafayette, Ind.

[21] Appl. No.: 09/156,459

[22] Filed: Sep. 18, 1998

Related U.S. Application Data

[63] Continuation-in-part of application No. 08/839,299, Apr. 17, 1997, Pat. No. 5,816,256.
[51] Int. Cl.[7] ............................. A61B 19/00; A01K 1/03
[52] U.S. Cl. ......................... 128/897; 119/421; 604/151; 604/247
[58] Field of Search .......................... 600/300; 128/897, 128/898; 119/417, 421; 604/131, 151, 152, 247, 250

[56] References Cited

U.S. PATENT DOCUMENTS

| | | | |
|---|---|---|---|
| 3,897,751 | 8/1975 | Gullino et al. | 119/15 |
| 3,999,519 | 12/1976 | Rodemeyer | 119/29 |
| 4,284,034 | 8/1981 | Belew | 119/17 |
| 5,345,943 | 9/1994 | Hargreaves et al. | |
| 5,419,312 | 5/1995 | Arenberg et al. | |
| 5,558,073 | 9/1996 | Pomeranz et al. | |
| 5,564,434 | 10/1996 | Halperin et al. | |
| 5,598,847 | 2/1997 | Renger | |
| 5,816,256 | 10/1998 | Kissinger et al. | 128/897 |

OTHER PUBLICATIONS

M.A. Parada, et al., Journal of Neuroscience Methods 60, Jan. 12, 1995, 133–139.
H. Matsumura, et al., Journal of Neuroscience Methods 57, Jun. 24, 1994, 145–149.
B. Greenstein, ed., Neuroscience Research Methods, Clark et al., vol. 1, Chapter 10, pp. 205–222.

(List continued on next page.)

*Primary Examiner*—Eric F. Winakur
*Attorney, Agent, or Firm*—Ice Miller Donadio & Ryan; Doreen J. Gridley; Michael A. Swift

[57] ABSTRACT

A movement-responsive system for conducting tests on freely-moving animals is disclosed. The invention includes a container for housing the animal, a mechanism for rotating the container in response to rotational movement of the animal, and one or more test leads connected to the animal for performance of biomedical tests such as infusion, in vivo ultrafiltration, laser-doppler monitoring of blood flow, electrical stimulation and in vivo microdialysis, and a method for automated micro sampling of body fluids in free-moving animals. Because the cage is rotated in response to the animal's rotational movement, no swivel connectors are needed. A rotational sensor assembly is provided to detect rotational movement of the animal within the container. A vertical sensor assembly is mounted to the counterbalanced arm for monitoring vertical movements of the animal. The outputs of the sensor assemblies are routed to a computer or other device for monitoring and/or analyzing the activity of the animal. The container is configured to act as an operant chamber or a metabolic chamber by locating a hole in the bottom of the container and through the rotating mechanism. The invention also enables a new method for sampling body fluids of the animal without restricting the animal's movements. The sampling method uses a syringe pump to result in high fidelity fluid control greatly increasing repeatability of experiments. Further, the method employs pinch valves to control fluid flow in conjunction with an anticoagulant coated tubing, thereby resulting in a blood sampling method that does not require the use of heparinized sterile saline solution as a wash fluid.

46 Claims, 14 Drawing Sheets

OTHER PUBLICATIONS

H2 Harvard Single–Station Operant Behavioral Lab Packages, Harvard Apparatus, Natick, MA., Brochure.

G2 Metabolic Cages for Rodents, Harvard Apparatus, Natick, MA., Brochure.

Complete Metabolic Chamber System, Kent Scientific Corporation, Litchfield, CT., Brochure.

H14 Activity Meters and Monitoring Systems, Harvard Apparatus, Natick, MA., Brochure.

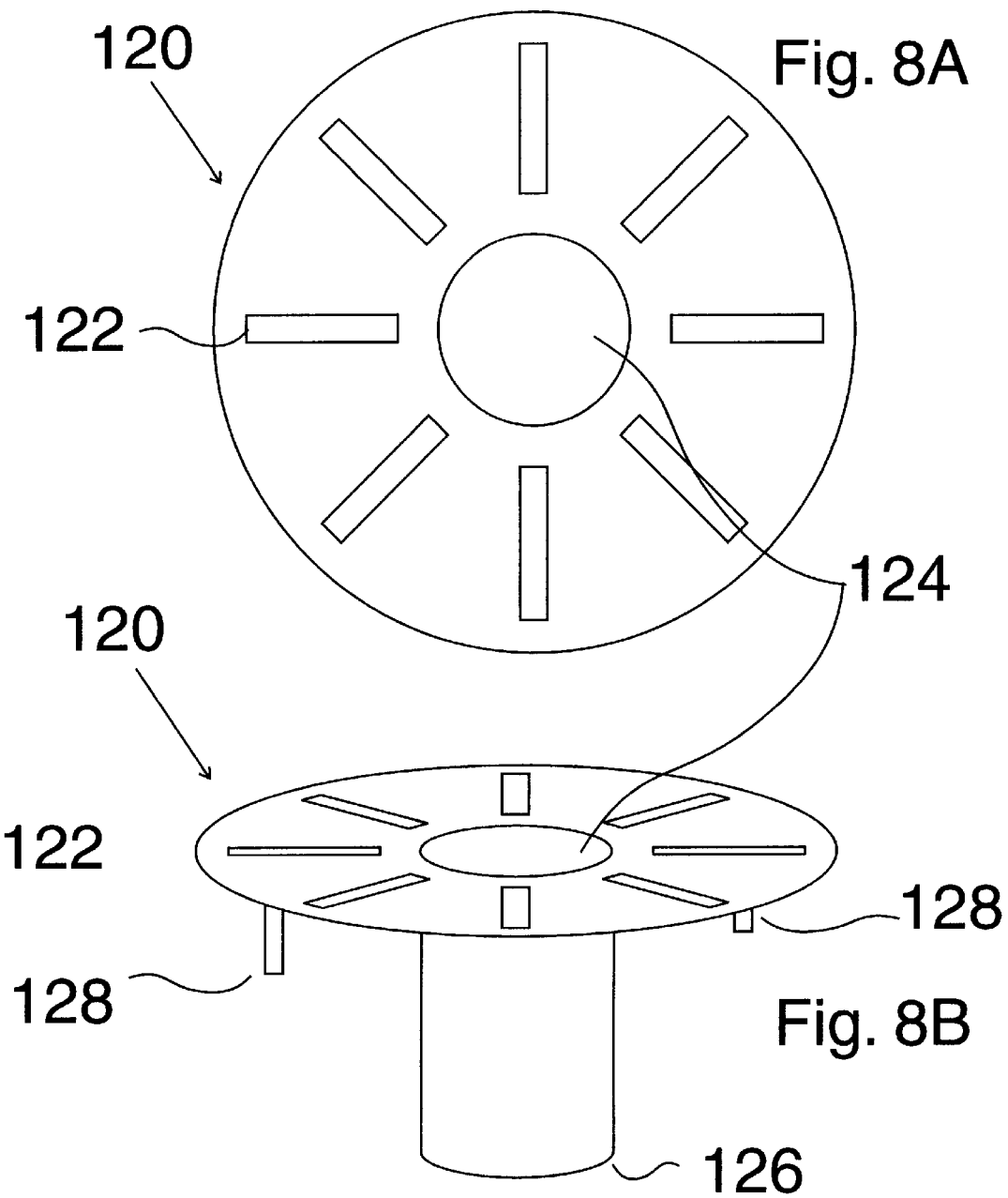
Fig. 8A
Fig. 8B
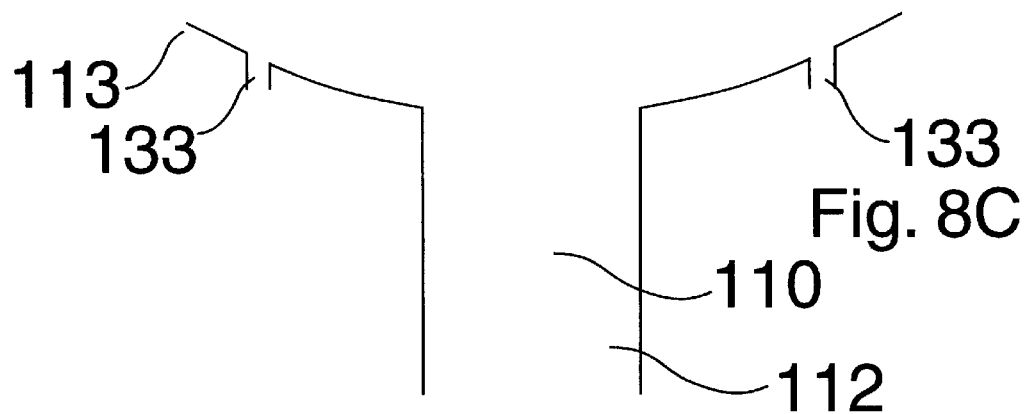
Fig. 8C

MOVEMENT-RESPONSE SYSTEM FOR CONDUCTING TESTS ON FREELY-MOVING ANIMALS

RELATED APPLICATIONS

This is a continuation-in-part of application Ser. No. 08/839,299 filed Apr. 17, 1997, now U.S. Pat. No. 5,816,256.

FIELD OF THE INVENTION

This invention relates to an apparatus for use in biomedical research, and, in particular, to a system for conducting infusions, electrophysiology, ultrafiltration, microdialysis, electrochemistry, pharmacokinetics (PK), drug metabolism, drug distribution, sampling of body fluids (e.g. bile, blood), optical fiber transmission and behavioral monitoring in conscious, freely-moving animals.

BACKGROUND OF THE INVENTION

Working with conscious animals is a requirement of important biomedical research techniques such as infusion, in vivo microdialysis, in vivo ultrafiltration, in vivo electrochemistry, biosensors and electrophysiology. All of these methods study the functioning of living organs such as the brain, heart, circulatory system, muscles, etc. They also involve connections between external devices such as syringe pumps, fraction collectors, electrometers, vacuum sources, light sources, and potentiostats to implants in the animal's body such as infusion cannula, ultrafiltration probes, microdialysis probes, or electrodes. In conjunction with these tests, it is sometimes desirable to monitor animal activity and/or feces and urine composition. The means of connection is typically a length of flexible, hollow, plastic tubing, a flexible wire, or an optical fiber.

Frequently, in the prior art, the connection of one or more lines of tubing for conveyance of fluids in such tests involves the use of a liquid swivel, or, for electric or optical leads, the use of a swivel-commutator (such as an electrocannular device). In general, a portion of the lead is connected to the top of the swivel which is mounted on a support above the animal, while an additional portion of the lead is connected from the implant on the animal to the underside of the swivel. Liquid swivels are designed so that the top and bottom half rotate independently and an internal seal connects the two halves. When the connection is electrical or optical, a form of commutator is required. For liquid swivels and swivel commutators, the lead is discontinuous, i.e., it is somehow "split" at the swivel, so that the bottom half of the lead may be required to rotate with respect to the top half of the lead.

Liquid swivels are frequently unreliable. Further difficulty in their employment results when there is a need to connect more than one tubing line, as in microdialysis. Multi-channel liquid swivels typically use concentric cannulae with concentric, complex seals separating each channel from the next. The seals wear easily when exposed to salty, physiological solutions. When they leak, cross-channel contamination is a common occurrence. Use of liquid swivels is also difficult when an electric or optical line (lead) is to be connected to the animal, for such an electric or optical lead requires the addition of a commutator to maintain contact with leads attached to the animal. Although the swivel and commutator can accommodate rotation of the respective leads, the leads, or a portion thereof, can become entangled when the leads rotate with respect to each other.

The use of a liquid swivel undesirably adds additional volume to a fluid path. For example, connecting tubing for microdialysis typically has an internal diameter of 0.12 mm. A length of 10 cm of such tubing contains a volume of approx. 1.2 $\mu$L of fluid. A two channel liquid swivel, such as the stainless steel model available from Instech Laboratories of Plymouth Meeting, Pa., has a dead volume of 1.4 $\mu$L for the center channel and 18.5 $\mu$L for the side channel. Thus, when such a swivel is used, it takes more time to transfer fluid the same distance due to the dead volumes of the channels. Consider a situation where the distance between the animal and a device such as a fraction collector is 30 cm, where the fluid travels at a rate of 2 $\mu$L per minute, and the height of the swivel is 5 cm. The volume in 30 cm of tubing is 3.6 $\mu$L, and it would take 1.8 minutes for the fluid to travel from one end to the other of this 30 cm tubing. A 5 cm long swivel and 25 cm of tubing would occupy the same distance, but the volume of this combination (using the center swivel channel of the Instech Laboratories tubing) would increase to 4.4 $\mu$L, and, thus, it would take 2.2 minutes for fluid to traverse this combination of tubing and swivel. If the side channel of the swivel was used, the volume would be 21.5 $\mu$L, and time for traversing the tubing and swivel would increase to 10.7 minutes.

The use of liquid swivels adds further limitations when the fluid within the system is blood. Use of liquid swivels generally requires the use of heparinized saline as a wash fluid for blood sampling since the swivel in contact with the blood leads to clotting in the absence of heparin. Consequently, blood serum testing is unavailable in a system utilizing a liquid swivel due to the presence of heparin. Additionally, the injection of heparinized saline into the animal affects the PK behavior of drugs and can lead to increased bleeding in the animal. If a method of blood sampling is used in which the animal is not injected with heparinized saline, there is a risk of dehydration of the animal, consequently, the blood sampling activity is significantly restricted.

The use of liquid swivels is common, as described above. The article "Triple electrical channels on a triple fluid swivel and its use to monitor intracranial temperature with a thermocouple" by Parada et al., Journal of Neuroscience Methods, Vol. 60 (1995), pg. 133–139, describes a complex liquid swivel which deals with the aforementioned limitations in fluid channels by creating an extremely complex device. It is desirable to avoid such a complex system, and to avoid the use of liquid swivels while permitting for free movement of the animal.

Another shortcoming of swivel systems relates to tracking the movement of the freely-moving animal. Rotational and vertical behavior in laboratory rodents are well-established indicators of neurochemical changes occurring in the animal during testing. The clockwise or counterclockwise preference of the animal, the frequency of such rotation, and similar information concerning the vertical movement of the animal are valuable data not available with the prior art liquid swivel systems. It is therefore desirable to provide a system which not only permits for rotation of the animal, but also which is capable of tracking the rotational and vertical movements of the animal for identification of behavioral changes occurring during testing.

The use of liquid swivels and commutators also results in additional manufacturing costs and in unwanted repair costs. Because the swivels naturally wear out during the course of normal use, continual repair or replacement of the swivel is required. It is preferred to avoid the use of swivels to avoid the extra expense thereof in manufacture and repair, but to maintain the ability to perform operant and metabolic testing of an animal with test leads connected.

An apparatus for infusion in a freely-moving animal is disclosed in U.S. Pat. No. 3,897,751, Gullino et al. The apparatus of Gullino et al. utilizes a continuous catheter to infuse the animal and permits for movement of the animal by threading the catheter between the walls of the cage and an elevated cover. Gullino et al. does permit for rotation of the animal by use of a spring. However, if such rotation were to occur, because of the inherent tension of a spring, stress is applied to the catheter. Such rotational stress could result in harm to the animal or may disconnect or impair the connection of the catheter to the source of fluid. Therefore, it is desired to provide an apparatus for infusion in a freely-moving animal which permits for the rotational movement of the animal while employing continuous leads which does not result in harm to the animal or disconnection or impairment of the connection of the lead to its source.

Another apparatus for conducting tests on freely-moving animals is described in a scientific article entitled "A novel apparatus that permits multiple routes for infusions and body-fluid collections in a freely-moving animal", Matsumura et al., Journal of Neuroscience Methods, Vol. 57 (1995), pg. 145–149. Matsumura et al. does disclose a movement-responsive apparatus which permits for rotation of the animal by rotating the floor of the cage housing the animal. Specifically, in the disclosed apparatus, multiple fluid lines are passed through the center of a device mounted to a fixed support above a cylindrical chamber. The animal is tethered to this device by the electrical lines. The electrical lines are connected through a slip-ring commutator on the exterior of the device. This type of connection means that the top and bottom half of the device rotated independently, like a swivel. The floor of the cylinder portion of the cage is moved in response to the animal's movement while the walls of the cage are immobile.

The apparatus of Matsumura et al. has several shortcomings, however. For example, the invention of Matsumura et al. permits full rotation of the animal through three, or more, complete 360° turns before responding to the animal's movement with counterrotation. This movement can create undesirable twisting and stress on the leads connected to the animal. In addition to the potential for equipment malfunctions, the twisting and stress can cause discomfort to the animal thereby altering the animal's behavior. Further, despite employment of a microcomputer, the apparatus of Matsumura et al. does not track rotational or vertical behavior of the animal—valuable indicators of neurochemical changes occurring in the animal during testing.

A method and apparatus for conducting automated microsampling of blood in conscious rodents is described in a scientific book entitled Neuroscience Research Methods, Clark et al., Vol. 1, Chapter 10, pages 205–222. Clark et al. teaches a method and apparatus for automated microsampling of blood which uses a Gilson Minipuls 3 peristaltic pump to withdraw blood from the animal through a sterile polyethylene catheter. The blood is then transported through nonsterile polyethylene tubing which is connected to the catheter using silastic tubing. Within the length of tubing is positioned a liquid swivel to permit the animal to rotate without twisting the tube. Lee valves are used in conjunction with the peristaltic pump to direct the blood sample to chilled open vials. In this example, the Lee valve is representative of a valve system in which the blood is in direct contact with valve components, in which the blood departs from the conducting tube when entering the valve, and in which blood returns to another conducting tube when exiting the valve. The use of polyethylene tubing, a swivel and Lee valves mandates the use of heparinized saline as a wash fluid to reduce the risk of clotting within the tube, the swivel, and the valves.

The method and apparatus of Clark et al. has several shortcomings. For example, the shortcomings associated with use of a swivel as discussed supra apply to Clark et al. Also, use of a peristaltic pump for control, is a high cost solution, partially due to the added costs for calibration of individual systems. The ability to precisely recreate certain experiments is limited due to volumetric errors associated with peristaltic pumps which deliver a pulsatile flow and are subject to degradation of the peristaltic tubes during use—a change which also affects flow rate. Additionally, sterile and non-sterile polyethylene tubes and catheters are subject to clotting. Once a tube or catheter is clogged, it must be removed, a replacement piece of tube or catheter must be cut, measured, and installed, and the system must be recalibrated. Further, silastic tubing connections are known to become loose resulting in leakage and/or clotting. More problems result from having valves in contact with blood. First, the potential for clotting exists. Second, once the valve is in contact with blood it cannot be conveniently re-sterilized. Consequently, the valve must be discarded after a single application. Finally, the use of heparinized saline as a wash fluid creates the risk of introducing heparin into the animal which can result in bleeding and can affect the PK behavior of drugs. Additionally, the presence of heparin eliminates the possibility of collecting blood serum since clotting is required in order to collect the serum by centrifuging.

Systems for monitoring the vertical activity of animals exist in the prior art. A typical system is embodied in the Harvard/Columbus Instruments Basic Activity Meters (Harvard apparatus, Natick, Mass.). These units use infrared sensor beams at spaced intervals in conjunction with a control unit to detect activity. These systems are bulky and expensive. More exotic units such as the Harvard/Columbus Instruments Activity Monitoring System (Harvard apparatus, Natick, Mass.) utilize an infrared scanner to monitor animal movements at even greater costs. It is desired to provide an apparatus for monitoring vertical movement in a freely moving animal which is inexpensive, compact and significantly less complex.

Accordingly, the avoidance of the use of a liquid swivel in a conscious animal monitoring system thereby results in the following advantages over the prior art:

Eliminates the severe limitation in the number of viable fluid channels connected to a test animal due to increasing friction loads as more channels are added to a liquid swivel which eventually render the swivel immobile;

Eliminates the need to compensate for and accommodate the extra system volume of a liquid swivel;

Imposes no restrictions on the number or combination of electrical, fluid or optical channels employed in the system;

Imposes no restrictions on the relative placement of different types of channels (e.g. electrical and fluid) used in the same monitoring system;

Eliminates the need to compensate for and accommodate the extra liquid travel time between the implant and the external device (pump, fraction collector, etc.) caused by a liquid swivel;

Avoids cross-contamination between channels that occurs in a liquid swivel which is capable of handling multiple fluids;

Avoids the extra expense from continual replacement or repair of swivels which naturally wear out during the course of normal use.

It is another advantage of the present invention to provide a movement-responsive system which tracks rotational and vertical behavior of the animal, while imposing no restrictions on operant or metabolic testing.

It is yet another advantage of the present invention to provide a system which does not require leads subject to rotational forces to be affixed to either the animal or the source or device to which the lead is connected to thereby avoid potential harm to the animal or of disconnection or impairment of the connection of the lead to the animal or to the source or device.

It is still another advantage of the present invention to provide sensor systems which are inexpensive to manufacture and which are highly reliable during operation.

Further, it is still another advantage of the present invention to provide a movement-responsive system which can be utilized for a myriad of biomedical tests performed on freely-moving animals, including but not limited to infusion, electrophysiology, blood monitoring, ultrafiltration, microdialysis, electrochemistry, optical fiber transmission, operant behavior, pharmacokinetics, bile sampling, automated micro blood sampling, and metabolic and behavioral monitoring and which permits for more than one such test to be performed concurrently.

Another advantage of the present invention is to provide a testing apparatus which does not result in undesirable change in the animal's behavior as results from some of the prior art systems.

An additional advantage of the present invention is to accommodate both the rotational and vertical movements of an experimental animal by use of a rotational sensor mounted on a counter-balanced arm and tether assembly which keeps leads out of the animal's reach, and reduces animal stress by minimizing collar tension.

It is also an advantage of the present invention to provide a method and apparatus for automated micro blood sampling which eliminates the use of heparinized saline solution while reducing the risk of clotting and leaking. This same apparatus can be used to sample other body fluids such as bile which can be removed from the bile duct and replaced with an equivalent volume of bile salts solution.

It is another advantage of the present invention to provide a system with these and other capabilities and features which is inexpensive to manufacture, repair and maintain.

SUMMARY OF THE INVENTION

The present invention comprises an apparatus for performing at least one biomedical test on a freely-moving animal. It is a reliable movement-responsive system which rotates the container in response to rotational movement of the animal in the container to avoid entanglement, crimping, disconnecting, or twisting the leads that are connected to the animal for testing purposes. In one embodiment, the apparatus comprises a container for housing the animal, a means for rotating the container in response to rotational movement of the animal, and at least one lead for performance of at least one biomedical test on the animal.

The apparatus in one embodiment comprises a container upwardly tapered from the bottom surface such that feces and urine are directed by the tapered lower section to the hole in the bottom surface of the container. The rotating means also has a hole which aligns with hole in the bottom surface of the container which allows urine and feces to pass further through the rotating means. The container further includes a means for separating the feces from the urine. The means for separating the feces from the urine separates and collects urine and feces to allow for metabolic testing. Additionally, the hole in the bottom surface of the container and the aligned hole in the rotating means may be used to pass a support means for a test mechanism, such as a push bar, into the container for purposes of operant behavior testing of the animal.

The rotating means includes a rotational sensing means which includes first and second close-ended, limit detectors and a triggering element having at least a portion thereof capable of activating the limit detectors. Analysis of the rotational movement of the animal is made possible by connecting an analysis means with the apparatus. The analysis means receives input from either the first and second limit detectors or from the rotating means. In either event, a signal is generated as a consequence of animal movement, with this signal providing a history of the rotational behavior of the animal.

The apparatus further includes a vertical sensing means which has an activating element responsive to the vertical movements of the animal and a vertical detection element positioned to detect the movement of the activating element. The vertical detection element is generally of the type to be activated by an interruption, reflection, or detection of a light beam, a magnetic field, a radioactive field, or a flow of gas or liquid to produce either analog or digital output. The activating means in one embodiment is the counterbalanced arm which moves in response to the animal's vertical movements. The vertical detection element produces an output indicative of the vertical position of the animal, or indicates the number of times the animal's vertical position passes through a predetermined point or points.

The apparatus of the present invention further includes at least one test lead for performance of at least one biomedical test. The lead has a first end for connection to the animal and a second end for connection to a device external to both the animal and the containment system. During operation, rotational movement of the animal causes the rotating element of the rotating means to trigger either the first or second limit detectors to thereby result in counter-rotation of the container. In addition, the rotating and rotational sensing means are mounted on a lever arm which responds to upward and downward movement of the animal through a counter-balanced weight which pulls the rotating and rotational sensing means, and all associated leads away from the animal (during upward movement) and with the animal (during downward movement). The lead is also connected to the vertical sensing means for activation of the activating element of the vertical sensing means in response to vertical movement of the animal.

One device external to both the animal and the containment system, but which can be used with the movement-responsive system, is an apparatus for conducting automated micro blood sampling (AMBS). The AMBS apparatus includes a means for conducting fluid, a means for receiving fluid, a means for moving fluid, fluid control means, and a sample collection control means. In one embodiment, the means for conducting fluid is resiliently compressible tubing, the means for receiving fluid is a refrigerated fraction collector having sealed vials for receiving blood samples, the means for moving fluid comprises a syringe pump, the fluid control means comprises pinch valves, and the sample collection control means comprises a personal computer (PC). Other acceptable sample control means include, but is not limited to, an electronic controller, timer, or other regulating device. The tubing provides communication between three areas, namely, the test animal, the refrigerated fraction collector and the syringe pump, which are connected through a three-way connector such as a "Y" or "T" connector. The pinch valves are located so as to control fluid flow to and from these three areas. The pinch valves associated with the tubing which connects the test animal and the refrigerated fraction collector may be combined within a common housing and utilize a common pinch bar so as to realize a three-way pinch valve which operates such that whenever one selected tube is open, the other is shut. In this embodiment, the test lead, tubing, and "T" connector have an anticoagulant coating. Since all surfaces in contact with the blood sample are coated, non-heparinized saline solution, which is sterile or not sterile, may be used as a wash fluid to flush the system and to move blood samples within the apparatus.

In one embodiment, the PC coordinates the pinch valve positions, fraction collector, and syringe activity so as to flush the system, withdraw a blood sample from the animal, move that blood sample to the refrigerated fraction collector, advance the fraction collector to the next vial position or waste, and inject back into the animal any non-used blood as well as an amount of saline equal to the blood sample taken. The PC can also effect the refilling of the syringe pump with sterile saline solution from a sterile saline solution supply means.

Other devices used to contain animals during infusions, microdialysis, blood flow monitoring, or electrical recording are complex and/or unreliable, and have one or more of the shortcomings discussed herein. The present invention offers a simple and reliable means of connecting a device implanted in or attached to an animal to an external controlling or monitoring device located at a distance from the animal which permits the animal to move freely during such biomedical testing. Some of the advantages of the present invention over the prior art are summarized as follows:

Connecting tubing, optical fibers, and wires (collectively referred to herein as "leads") to are not broken. They remain as a single, unbroken piece connecting the implanted device to the external device.

When tubing must be broken to allow for multiple paths such as is the case in automated micro blood sampling, tubing and connectors which are easily coated with an anti-coagulant can be used, eliminating the need for heparinized sterile saline solution.

Multiple leads can be used with no risk of cross-contamination since they are not joined or connected through a swivel, commutator or other junction.

Electrical wires and/or optical fibers can be used at the same time as tubing lines filled with fluid.

The rotational sensor assembly differentiates between clockwise and counterclockwise rotation by the animal and moves the animal, in its cage, in the opposite direction.

The vertical sensor assembly provides an inexpensive and reliable means for detecting vertical movement of the animal.

Signals from the rotational sensing means and the vertical sensing means can be recorded by a simple strip chart recorder or device such as a computer. These signals record the overall activity of the animal, its clockwise and/or counterclockwise movement and vertical movement.

The rotational sensor assembly is mounted on a counterbalanced arm so that slack in tubing or wires is taken up and away from the animal. This also creates less stress for the animal since the system responds to its vertical movements. Further, the system is not likely to cause behavioral changes in the animal.

The container can serve as an operant behavior and/or a metabolic container.

The AMBS apparatus can be used without heparinized saline allowing blood serum testing while eliminating effects on PK behavior of drugs or potential for bleeding.

The automated micro body fluid sampling apparatus uses syringe pumps which provide more precise control over sampling evolutions, thereby reducing errors and giving a higher degree of repeatability than prior art systems.

The automated micro body fluid sampling apparatus uses a personal computer or other controlling device to automate the sampling process thereby realizing simplicity in setup, expanded control options, expanded data collection possibilities, and expanded data presentation alternatives. These expanded capabilities include the potential for real time display of experiment results on the internet.

The automated micro body fluid sampling apparatus makes it possible to do several different types of experiments in a concurrent fashion, instead of in a serial or stepwise fashion, thus saving the researcher time and laboratory space.

BRIEF DESCRIPTION OF THE DRAWINGS

FIG. 8A and FIG. 8B show a top view and a perspective view, respectively, of one embodiment of the means for separating the feces from the urine, and FIG. 8C shows a partial cross-sectional view of one embodiment of the container of the present invention for receipt of the separating means shown in FIG. 8A and FIG. 8B;

DETAILED DESCRIPTION

Figure 1:
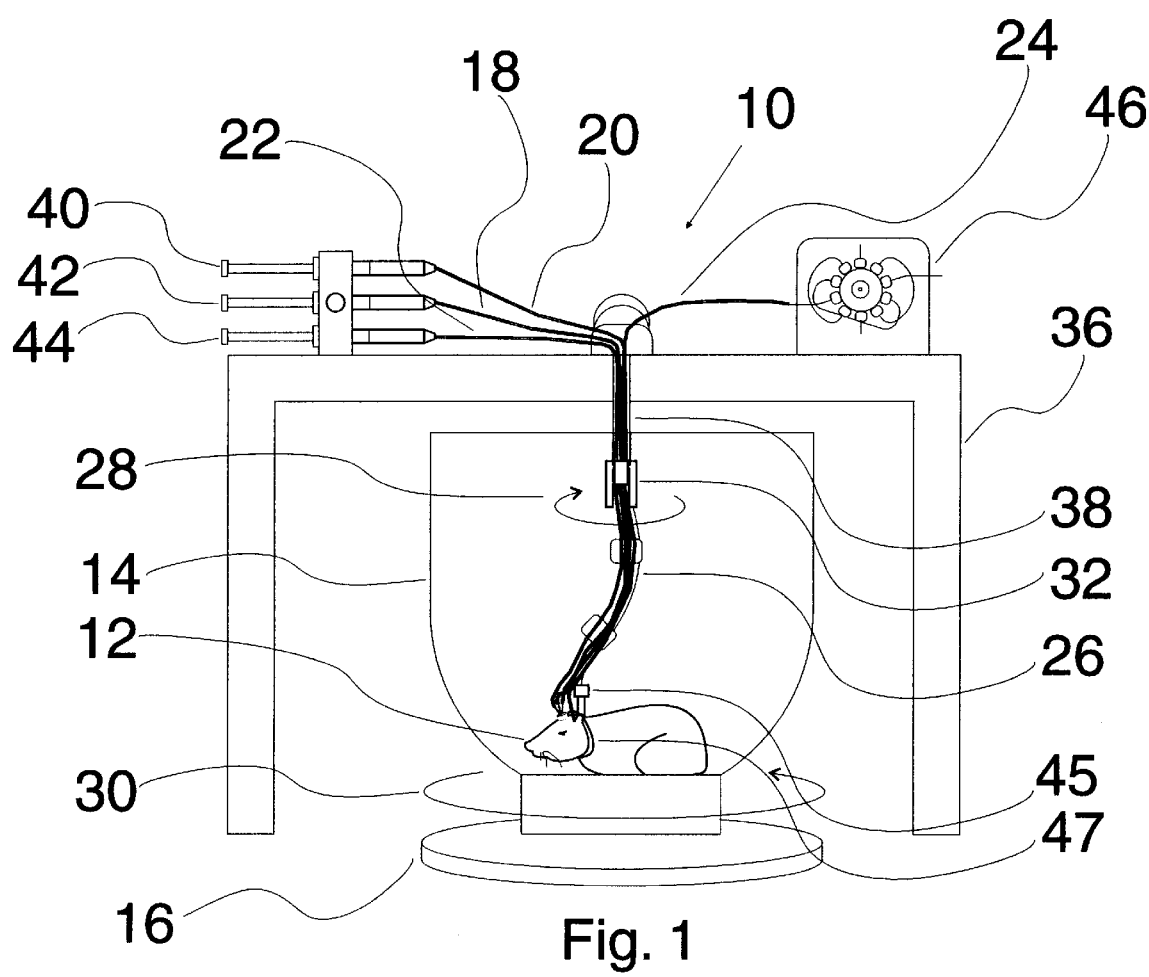
FIG. 1 shows a side view of one embodiment of the apparatus of the present invention.

Referring now to FIG. 1, there is shown a side view of one embodiment of the apparatus of the present invention. Specifically, in this embodiment, movement-responsive test system 10 is capable of performing biomedical tests on animal 12, which in this embodiment is a laboratory rat. Animal 12 is housed within cage or bowl 14 during performance of the biomedical test(s). Cage 14 is more thoroughly described in association with FIG. 3, FIG. 4, FIG. 6, FIG. 7 and FIG. 10 hereof, and is connected to powered turntable 16 as is described in association with FIG. 2 hereof. Animal 12 is connected to test leads 18, 20, 22 and 24 and to tether line 26 as is described in greater detail herein.

The primary objective of system 10 is to provide an apparatus which is responsive to the rotational movement of animal 12 during biomedical testing. More specifically, if animal 12 rotates in the direction indicated by animal movement arrow 28, system 10 causes turntable 16 and cage 14 to rotate in the direction indicated by cage movement arrow 30. Similarly, if animal 12 were to rotate in a direction opposite that of animal movement arrow 28, system 10 causes turntable 16 and cage 14 to rotate opposite the direction indicated by cage movement arrow 30. In other words, system 10 causes cage 14 to rotate in the counter-rotation direction of the detected direction of rotation of animal 12. In this manner, test leads 18, 20, 22, and 24 and tether line 26 do not become twisted or entangled upon rotation of animal 12.

To accomplish this objective, system 10 includes a means for rotating cage 14 in response to rotational movement of the animal, including sensor assembly 32 for sensing movement of the animal, a means for driving rotation of cage 14 in the appropriate counter-rotational direction (see motor 34 on FIG. 2, FIG. 4, and FIG. 5), and tether line 26 for connecting animal 12 to sensor assembly 32. Sensor assembly 32 is positioned and suspended above animal 12 in cage 14 by a support means comprising support table 36 having counterbalanced arm 38 pivotally mounted thereon. The use of counterbalanced arm 38 is desirable to take up slack in and to keep leads 18, 20, 22, and 24 and tether line 26 out of the animal's reach and yet allow the animal flexibility of vertical movement without placing unwanted stress on leads 18, 20, 22 and 24 or tether line 26.

In the embodiment of FIG. 1, first lead 18, second lead 20, and third lead 22 all comprise fluid tubing implanted in the head of animal 12 at one end. The other ends of first, second and third leads 18, 20, and 22, extend through sensor assembly 32 (see FIG. 4) and are connected to first, second and third syringe pumps 40, 42, and 44, respectively, for delivery of fluids to animal 12. Fourth lead 24, also tubing, is also implanted at one end in the head of animal 12, and is connected to electrically-activated injection valve 46 at its other end for collection of fluid from a probe implanted in animal 12. This fluid would subsequently be injected into a liquid chromatography or mass spectrometry system for analysis. It is important to note that the present invention permits for each lead 18, 20, 22 and 24 to be continuous, i.e., to have no breaks or seals therein.

Figure 4:
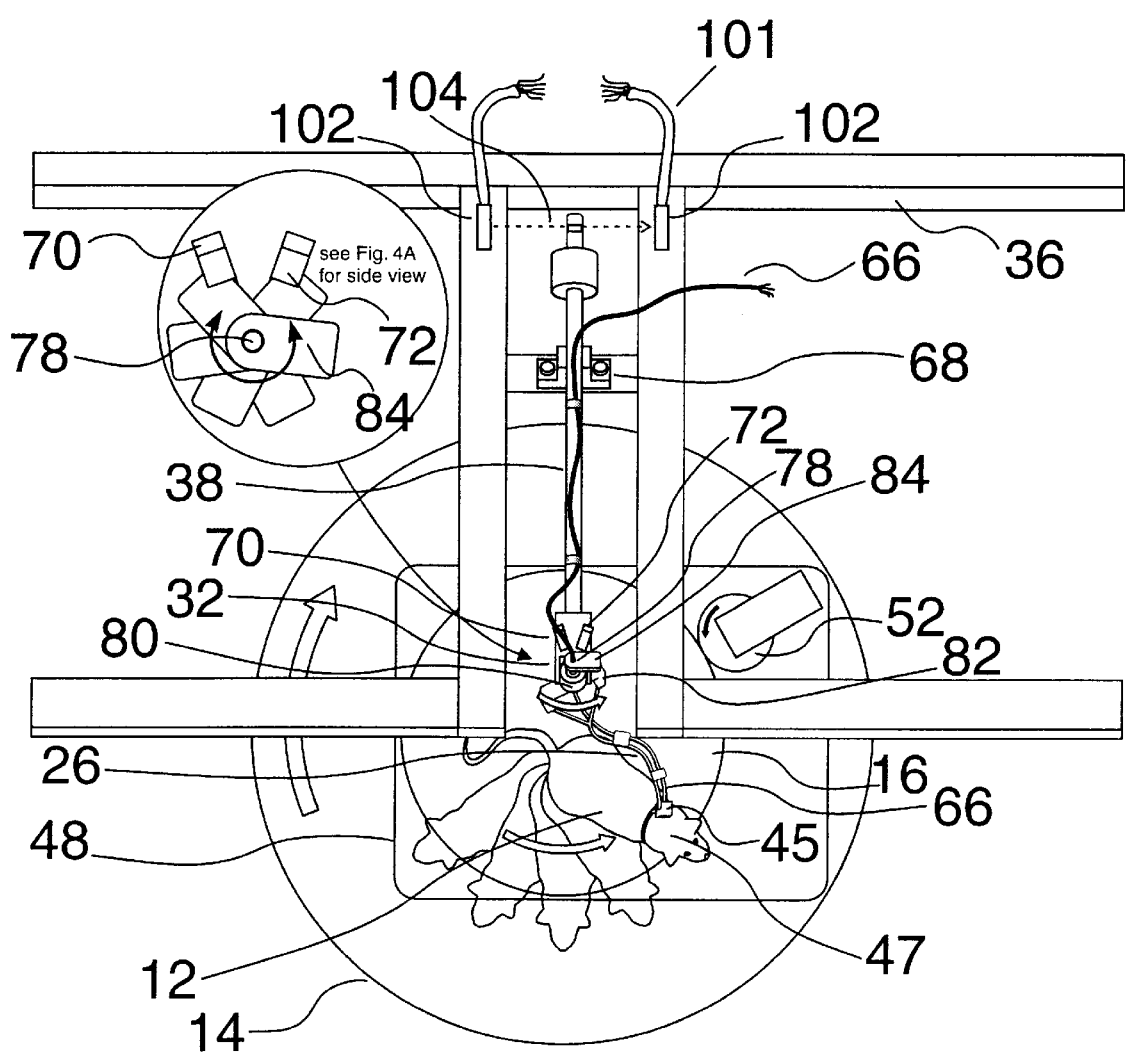
FIG. 4 shows a top view of the embodiment of the apparatus of the present invention illustrated in FIG. 1, except that all leads are gathered in a single bundle.

One end of tether line 26 is attached by means of a clamp 45 to animal 12 by collar 47. Collar 47 is essentially a belt which is non-invasively fastened about the neck of animal 12. The other end of tether line 26 is connected to sensor assembly 32 as shown in FIG. 4.

Also contemplated to be within the scope of the invention are leads which comprise electric lines for the receipt or transmission of electric signals, and optic fibers for the receipt or transmission of light signals. Such lines are illustrated in the bundle shown in FIG. 4. Also, tether line 26 may be a wire, spring, cable and the like and be within the scope of the invention. Further, cage 14 is essentially a container which restricts the animal's movement during test. Platforms or other enclosures are envisioned to be within the scope of the invention.

Figure 2:
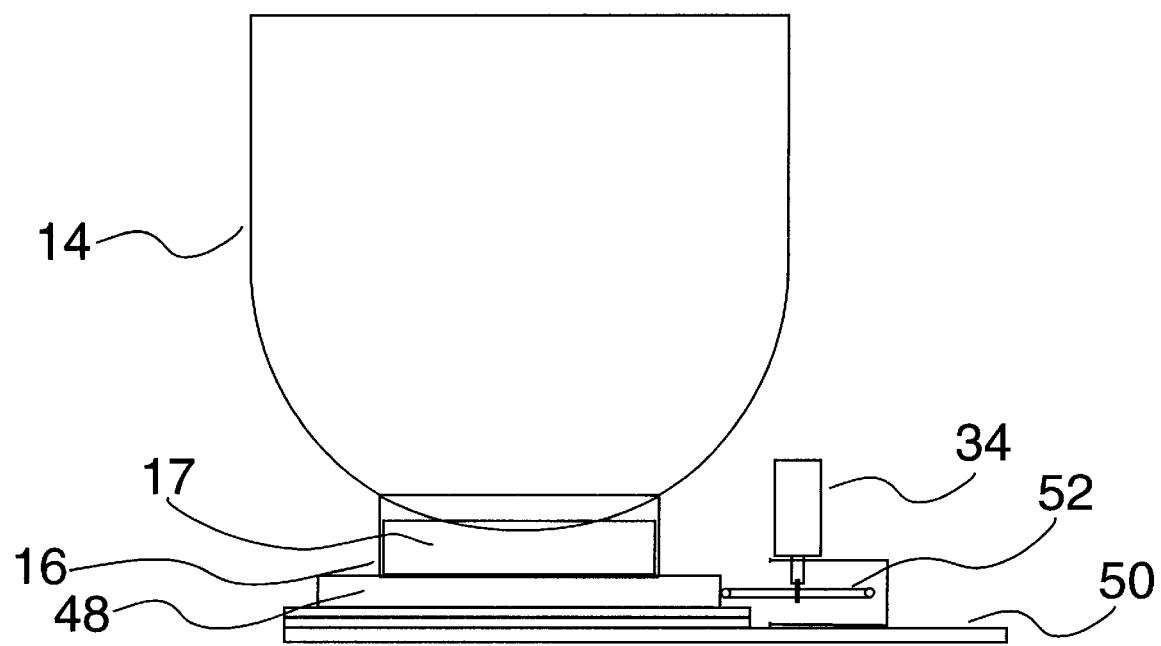
FIG. 2 shows two side views of one embodiment of the cage of the present invention, both disassembled and connected to the turntable and the electric motor for driving the turntable.

FIG. 2 shows two side views of one embodiment of the cage of the present invention, both disassembled and connected to the turntable and the electric motor for driving the turntable. Bowl 14 rests on turntable 16 as illustrated. Specifically, bowl 14 is a round bottom bowl, and may be comprised of translucent material, such as plexiglass. To permit bowl 14 to stand and be stable, affixed, such as by glue, to the bottom exterior surface of bowl 14 is ring or bowl base 15. Bowl base 15 may also be comprised of a material such as plexiglass. Rotatable turntable 16 is placed on, and rotates with respect to, surface 48. To keep bowl 14 in contact with turntable 16 during rotation, in this embodiment, plate 17 is attached to turntable 16. Plate 17 is sized to contact the interior to circumference surface of bowl base 15 to hold bowl 14 in place. Drive wheel 52 of motor 34 engages turntable 16 to cause turntable 16, plate 17, bowl base 15, and cage 14 to rotate simultaneously. In this embodiment, motor 34 may be any reversible 12-volt DC motor, for example, and turntable 16 may be any suitably sized turntable ranging from the types used in phonographs to the types used for household kitchen cabinets.

It will be appreciated by those of skill in the art that the combination of the drive mechanism (motor 34 and turntable 16) with cage 14 permits for easy separation of cage 14 from the rest of system 12. Further, removal of collar 47 and/or clamp 45 from animal 12 facilitates removal of both animal 12 and cage 14 from system 10 as may be desired for cleaning of cage 14 or removal of animal 12 from connection to the system.

It will also be appreciated that rotation of the entire cage 14 is advantageous over an arrangement in which only the floor of the cage rotates. Rotating the cage and its contents at the same time as the animal makes this arrangement less disturbing to the animal as it would not appear to the animal that its food and water dispensers are rotating away from the animal as would be caused by rotation of only the cage floor. By rotating the entire cage 14, water and food attached to the walls of cage 14 also rotate. Thus, the animal is not likely to learn behavior to compensate for the rotation of the floor only as in the prior art. It is undesirable to modify the animal's behavior to during testing. Also, a more stable environment is created for animal 12 and the possibility that bedding or other materials in cage 14 or animal 12 itself will become caught between portions of a cage that rotate and portions that do not rotate is eliminated with the present invention.

Figure 3:
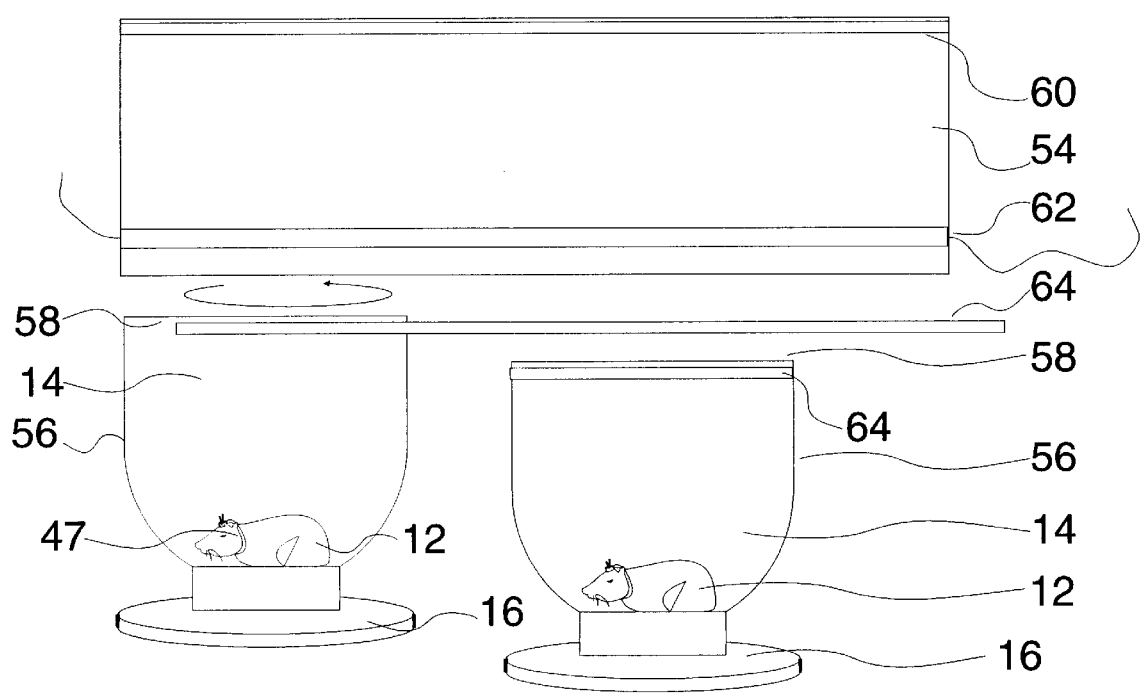
FIG. 3 shows a side view of one embodiment of the cage and cage cover of the present invention.

Referring now to FIG. 3, there is shown a side view of one embodiment of the cage and cage cover of the present invention. As in the embodiment of FIG. 1, cage 14 of this embodiment comprises a round-bottom bowl made of translucent or transparent material such as plastic, plexiglass, or glass. The shape of bowl 14 prevents casual contact between leads 18, 20, 22 and 24 and tether line 26 and the interior walls of bowl 14. The use of such materials permits an observer to view animal 12 while animal 12 is in cage 14 or inserted into or removed from cage 14. It may be desirable, however, for some biomedical tests, to cover cage 14 to reduce the sensation of movement experienced by the animal 12 during rotation of cage 14 by eliminating stationary visual cues residing outside cage 14.

To accomplish this objective without requiring cage 14 to be made of a non-translucent material, cage cover 54 is provided for removable connection to cage 14. Cover 54 is made of a non-translucent, flexible material, such as dark colored cloth or flexible plastic. Cover 54 is rectangular in shape and is of a length sufficient to cover the top edge 58 of cage 14. Attached near one edge of the length of cover 54 is at least one fastener 60, which in this embodiment comprises a strip of do the hooked portion of a VELCRO™ fastener running the entire length of cover 54. Near the opposing edge of cover 54 is a drawstring fastener 62.

Attached to bowl 14 near its top edge 58 is at least one mating fastener 64, which in this embodiment comprises the loop portion of a VELCRO™ fastener. Mating fastener 64 is positioned for fastening to fastener 60 of cover 54 so that when cover 54 is so fastened to bowl 14, cover 54 substantially covers the entire exterior surface walls 56 of bowl 14 around the entire circumference thereof. To engage cover 54 against exterior surface walls 56 at the bottom of bowl 14, drawstring fastener 62 may be drawn and tied.

Other types of fasteners other than a single length of VELCRO™ fastening material or a drawstring are contemplated to be within the scope of the invention. Other fasteners may include snaps, rivets, magnetic strips, zippers, elastic seams, or adhesive, for example. Further, cover 54 may be of a different shape than the rectangular shape shown in FIG. 3. It is possible, for example, to shape cover 54 so that no drawstring fastener 62 is required.

FIG. 4 shows a top view of the embodiment of the apparatus of the present invention illustrated in FIG. 1, except that all leads are gathered together in a single bundle. Specifically, leads including fluid tubing, electric lines and optic fibers are bundled together in lead bundle 66. The external devices to which these leads are connected are not illustrated in this FIG. 4. As shown in this FIG. 4, sensor assembly 32 is connected to counterbalanced arm 38. Counterbalanced arm 38 is pivotably connected to support table 36 at pivot 68, thus permitting sensor assembly 32 to move up and down with respect to cage 14 and turntable 16. As previously stated, this support means for sensor assembly 32 takes up slack in lead bundle 66 and tether line 26, and keeps lead bundle 66 and tether line 26 above and out of the reach of animal 12, while permitting animal 12 to move vertically within cage 14 without placing undesired stress on lead bundle 66, tether line 26, or the ends thereof connected to animal 12 or to the external device (such as syringe pumps 40, 42 and 44 and injector 46 shown in FIG. 1).

Sensor assembly 32 comprises first and second limit detectors in the form of optical sensors 70 and 72, respectively, connected to counterbalancing arm 38. First and second optical sensors are of the type which emanate a light beam in the direction of paths 71 and 73, respectively (see FIG. 4A), and which are activated upon interruption of the respective light beam. In this embodiment, first and second limit detectors 70 and 72 are LED type optointerrupters, and may be Motorola Corp.'s model no. H21, for example. Sensors 70 and 72 are set at a predetermined angle with respect to each other, the significance of which is discussed later herein. The angle is a rotational measurement between sensors 70 and 72 with respect to the triggering element (second bracket 84) as described below. Further, first and second limit detectors 70 and 72 are close-ended, each having stop 87 and 89, respectively, which are discussed in greater detail herein in association with FIG. 4A.

Sensor assembly 32 also comprises hollow tube 78 within ball bearing 80 which is attached to arm 38 to permit hollow tube 78 to rotate while attached to counterbalancing arm 38 and in the same direction as animal 12 rotates, whether clockwise or counterclockwise. Lead bundle 66 passes through hollow tube 78 in the center of ball bearing 80 so that rotation of hollow tube 78 does not result in rotation of lead bundle 66 or the leads within lead bundle 66.

The center of rotation of hollow tube 78 is strategically positioned in this embodiment. Specifically, the axis of rotation of hollow tube 78 permits for intersection by second bracket 84 of both light beams of first and second optical sensors 70 and 72 for activation of the respective sensor 70 or 72 as described herein.

Attached at one end of hollow tube 78 is first bracket 82, and attached at the other end of hollow tube 78 is second bracket 84. Thus, first and second brackets 82 and 84 and hollow tube 78 all rotate together when a rotational force is applied thereto to cause hollow tube 78 to rotate within ball bearing 80. First bracket 82 is positioned so that no portion thereof triggers either beam emanating from first and second sensors 70 and 72, and, in this embodiment is located below limit detectors 70 and 72. Tether line 26 is connected to first bracket 82 such that rotational movement of animal 12 causes rotation of first bracket 82, hollow tube 78, and second bracket 84.

Figure 4A:
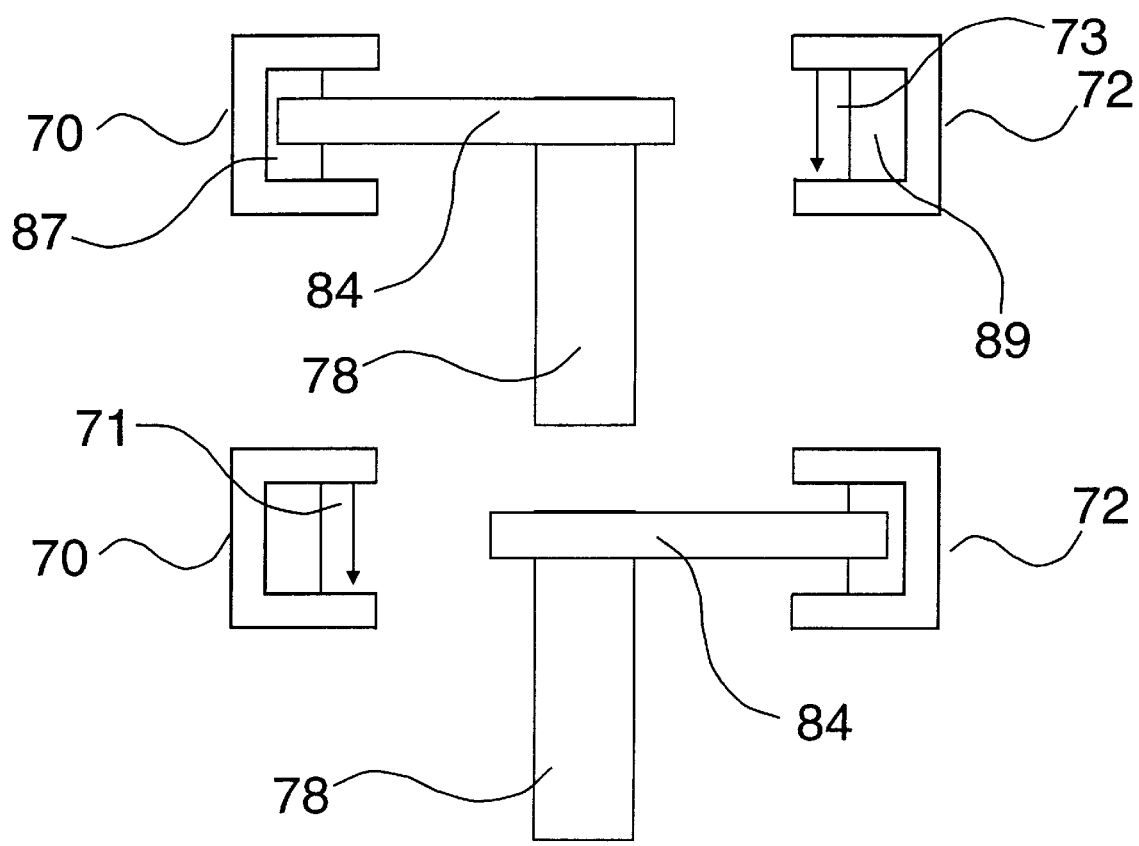
FIG. 4A shows side views of the limit detectors and triggering element of the embodiment of FIG. 4 to illustrate activation of the limit detectors.

As shown in FIG. 4A, second bracket 84 has a portion thereof which is capable of intersecting light beams emanating from first and second sensors 70 and 72 in paths 71 and 73, respectively. Specifically, second bracket 84 is a bracket with the first leg of second bracket 84 positioned so as not to intersect light beams of sensors 70 and 72. The axis of rotation of hollow tube 78, first bracket 82 and second bracket 84 extends through the first leg. The second leg has at least a portion thereof capable of intersecting the light beams of sensors 70 and 72 at or near the positions shown in FIG. 4A. In this manner, upon rotation of the second bracket 84, the second leg of second bracket 84 interrupts the light beams emanating from first and second sensors 70 and 72 at various points—one point for each light beam.

As shown in FIG. 4A, by virtue of the fact that first sensor 70 includes first stop 87 and second sensor 72 includes second stop 89, first and second sensors 70 and 72 are "close-ended". The second leg of second bracket 84 is stopped by the respective stop means 87 or 89 of sensors 70 or 72 so that second bracket 84 cannot rotate through the U-shaped interior of sensors 70 and 72. Thus, first and second sensors 70 and 72 are either activated or deactivated, and when a close-ended limit detector, such as sensors 70 and 72 are activated, it cannot be deactivated except by reversal or cessation of the rotational motion of second bracket 84 (and hence reversal or cessation of the rotational movement of animal 12). When a close-ended limit detector is deactivated, it cannot be activated until second bracket 84 is rotated, as by rotation of animal 12, to cause second bracket 84 to trigger the limit detector.

The use of opto-interrupter sensors disclosed in this embodiment represents one of many possible "limit detectors" which can be used in the present invention and are contemplated to be part of the present invention. The limit detector can be activated by an interruption or reflection of a light beam, a magnetic field, a radioactive field, a flow of air or liquid, or a simple contact with a microswitch, pressure sensitive button, magnet, electrical contact wire, or other mechanism. Thus, "triggering elements" other than the rotating element of this embodiment are also contemplated to be within the scope of the present invention. As previously stated, the limit detectors are to be close-ended, and the triggering element must be such that it activates the limit detectors in response to rotational movement of the animal. Thus, the triggering element may be rotational, such as second bracket 84, or may be any other mechanism appropriate to activate the limit detector, including but not limited to a linearly moving device. For example, the limit detectors may be limit switches activated by a triggering element which comprises linearly-moving markers strategically located on a lead screw. When triggering element is not rotational, the rotational movement of animal 12 through tether 26 must be connected, by means well known in the art to the non-rotational movement of the triggering element. The key is that the sensor, also referred to herein as a "limit detector", is close-ended and thus results in simple electronic control as is hereinafter described.

Returning to FIG. 4, there is also shown a vertical sensing means which, in this embodiment, comprises vertical sensor assembly 101 which is responsive to vertical movement of animal 12. Vertical sensor assembly 101 includes a third limit detector in the form of optical sensor 102 and an activating element which in this embodiment is provided by counterbalanced arm 38. Optical sensor 102 is of the type which emanates a light beam in the direction of path 104 (see FIG. 4), and which is activated upon interruption of the light beam. In this embodiment, optical sensor 102 is an LED type opto-interrupter, and may be Model No. H21 made by Motorola, for example. Movement of counterbalanced arm 38 through path 104 thus activates optical sensor 102.

The embodiment disclosed represents one of many possible detectors which can be used in the present invention. In addition to the types of detectors mentioned in conjunction with detecting rotational movement (limit detectors), proximity or position detecting devices using similar principles are within the scope of the present invention. In addition to the linearly moving activating element (counterbalanced arm 38) disclosed, other forms of activating elements, including but not limited to rotational devices are envisioned to be within the scope of this invention. For instance, the activating element may form part of counterbalanced arm 38 at pivot 68, and pivot 68 may comprise the sensing device providing output reflective of the rotational position of counterbalanced arm 38 within pivot 68. In selecting the vertical sensing means to be utilized, it is important to consider the effect of the vertical sensing means on the movement of counterbalanced arm 38. If the vertical sensing means significantly dampens movement of counterbalanced arm 38, such as by friction, such dampening of counterbalanced arm 38 may negatively affect the benefits of counterbalanced arm 38 and also have a deleterious effect on the sensitivity of the vertical sensor.

Figure 5:
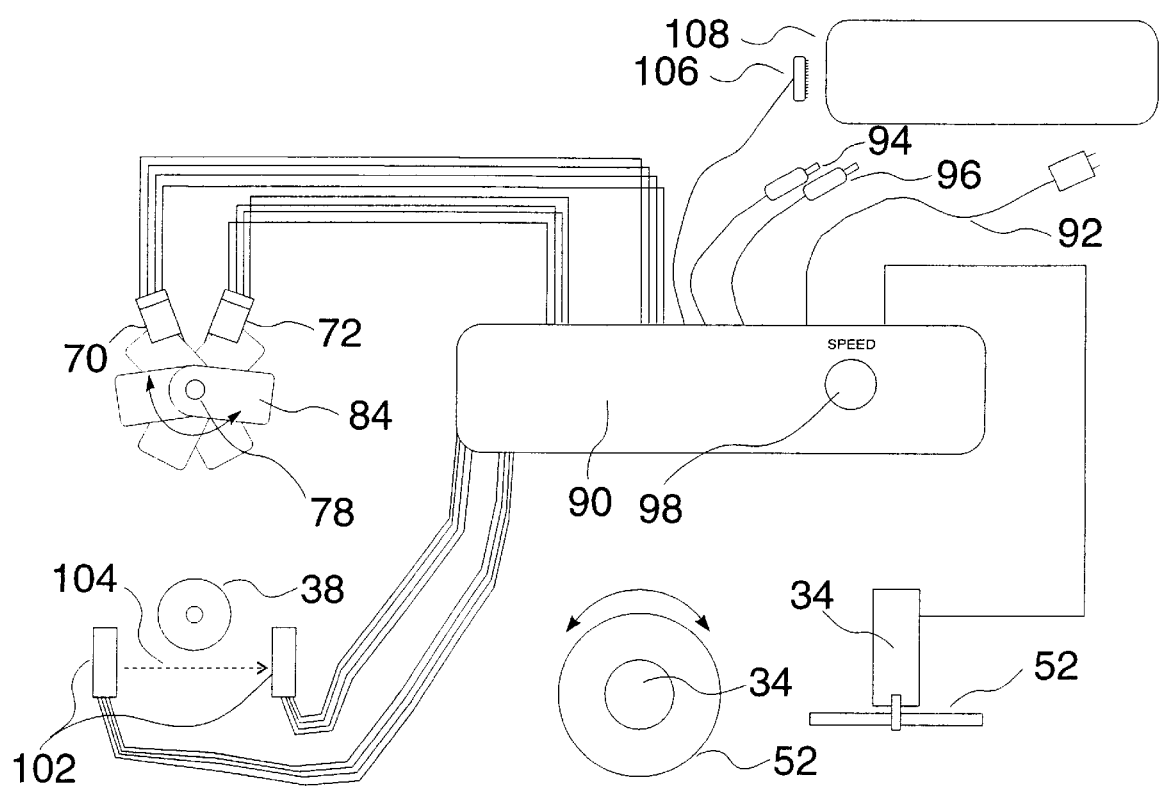
FIG. 5 shows a block diagram of the electronic components of the embodiment of FIG. 1 and FIG. 4.

Referring now to FIG. 5, there is shown a block diagram of the electronic components of the embodiment of FIG. 1 and FIG. 4. In general, the electronic components of system 10 includes first, second, and third sensors 70, 72, and 102, analog controller 90, and motor 34. Electric power is supplied to all components through power cord 92 to analog controller 90. Each optical sensor 70, 72, and 102 has four wires extending therefrom and connected to analog controller 90 as illustrated. Two of such wires are used for provision of power, and two of such wires are for the activation signal of applicable sensor 70, 72, and/or 102. Analog controller 90 also includes output leads 94, 96, and 106 for connection to a recorder or computer 108 to track and analyze the direction and duration of rotation and vertical activity of the animal based on which of optical sensors 70, 72, and/or 102 is activated and the frequency and duration of such movements. Analog controller 90 also includes speed control 98 which comprises a potentiometer for varying the power level sent to motor 34 to thereby vary the speed of rotation of motor drive wheel 52.

Referring now collectively to FIG. 1, FIG. 4, and FIG. 5, the operation of system 10 will now be described. Up and down motion of animal 12 does not result in rotation of cage 12. Rather, such vertical movement is compensated for by counterbalanced arm 38 which also moves vertically in response thereto.

If animal 12 rotates in a clockwise or counterclockwise direction in cage 14, cage 14 is caused to rotate in the counter-rotational direction in response thereto. Specifically, when animal 12 rotates, first bracket 82 is caused to rotate by the connection of tether line 26 to animal 12 and first bracket 82. Second bracket 84 is caused to rotate by rotation of hollow tube 78 about its axis of rotation and about lead bundle 66 (or leads 18, 20, 22, and 24 in FIG. 1), but without rotating lead bundle 66 (or leads 18, 20, 22, and 24 in FIG. 1). Rotation of first bracket 82 also results in rotation of second bracket, or rotating element 84. The portion of rotating element 84 capable of intersecting the light beams of first and second optical sensors 70 and 72 will eventually activate either first sensor 70 or second sensor 72 by interrupting the respective light beam emanating therefrom.

Activation of first sensor 70 or second sensor 72 results in receipt of a respective activation signal by analog controller 90. Analog controller 90 determines the polarity of the signal to be sent to motor 34 based on whether first sensor 70 or second sensor 72 has been activated. Analog controller 90 then sends the polarity signal, the amplitude of which may be adjusted by speed control to 98, to motor 34 to cause motor drive wheel 52 to rotate in the desired direction and at the desired speed. Rotation of motor drive wheel 52 results in rotation of turntable 16 and cage 14 in a direction opposite of the direction of rotation of animal 12. Rotation of container 14 turns animal 12 and tether line 26, and, in turn, first bracket 82, hollow tube 78, and second bracket 84. As second bracket 84 exits sensor 70 or 72 (such as by reversal or cessation of the rotation of animal 12), the respective light beam is restored and the signal to controller 90 terminates, thereby shutting down motor 34 and the movement of turntable 16.

Activation of first sensor 70 or second sensor 72 by rotating element 84 also causes the respective sensor, first sensor 70 or second sensor 72, to send a signal down its respective output lead 94 or 96 to computer 108. Computer 108 logs the event as an activation. When rotating element 84 exits sensor 70 or 72 as described above, the signal sent by first sensor 70 or second sensor 72 down its respective output lead 94 or 96 to computer 108, terminates. Computer 108 logs this event as a deactivation. As is well known to one skilled in the art, software or hardware residing in computer 108 is then utilized to determine the number of activations and the sensor that was activated. Additionally, computer 108 may include a timer to log the time of activation and deactivation. Computer 108 thereby determines the duration of each activation of sensor 70 or 72 by subtracting from the time activation was logged the logged time that activation stopped. As is well known to one skilled in the art, the rotational behavior of animal 12 can also be displayed as a time history of activity.

In the embodiment of FIG. 5 with directions determined by viewing from above as in FIG. 5, if animal 12 rotates in a counterclockwise direction, rotating element 84 rotates in a counterclockwise direction thereby activating second sensor 72. Activation of second sensor 72 results in a motor signal from analog controller 90 having a polarity to cause drive wheel 52 of motor 34 to rotate in a counterclockwise direction. The attached computer will log the beginning of rotational activity in the counterclockwise direction based on the activation of second sensor 72. Counterclockwise rotation of drive wheel 52 causes turntable 16 and cage 14 to rotate in a clockwise direction—opposite of the direction of rotation of animal 12.

Similarly, if animal 12 rotates in a clockwise direction, rotating element 84 rotates in a clockwise direction to thereby activate first sensor 70. Activation of first sensor 70 results in a motor signal from analog controller 90 having a polarity to cause drive wheel 52 to rotate in a clockwise direction. The attached computer will log the beginning of rotational activity in the counterclockwise direction based on the activation of first sensor 70. Clockwise rotation of drive wheel 52 causes turntable 16 and cage 14 to rotate in a counterclockwise direction.

As previously mentioned, first and second sensors 70 and 72 are positioned at a predetermined angle with respect to each other as measured with respect to rotating element, second bracket 84. In FIG. 4 and FIG. 5, the angle illustrated is approximately 314°. It will be appreciated that this angle need not specifically be set at this value, but rather, the angle does impact the sensitivity of the sensor assembly, i.e., adjustment of the angle between first and second sensors 70 and 72 will render the system more or less responsive to rotational movement of animal 12. Specifically, if first and second sensors 70 and 72 are moved closer together (an angle smaller than 314°), rotating element 84 will interrupt the light beams and activate sensor 70 and 72 more frequently thereby increasing the sensitivity of system 10 to rotational movement of animal 12. If sensors 70 and 72 are further apart (an angle larger than 314°), rotating element 84 will activate sensors 70 and 72 less frequently thereby reducing the sensitivity.

If the triggering element used in the present invention is not a rotational element such as second bracket 84, but rather is linear, the limit detectors' predetermined position is measured with respect to the spacing between the activatable portions of the sensor. Still, the sensitivity of the sensing means (combination of the limit detectors and the triggering element) may be adjusted by adjusting the spacing between the limit detectors with the effect of increasing or decreasing the spacing akin to modification of the angle.

In the embodiment of FIG. 4, if animal 12 rears, tether line 26 attached by means of a clamp 45 to animal 12 by collar 47 will rise causing counterbalanced arm 38 attached to tether 26 to rotate about its pivot 68. The rotation of counterbalanced arm 38 about its pivot 68 causes the end of counterbalanced arm 38, as seen in FIG. 5, to descend, passing through optical sensor 102 and interrupting the light emanating in the direction of path 104. The interruption of light causes optical sensor 102 to be activated and sends a signal through its output lead 106 to computer 108. Computer 108 logs the activation as a single event.

Similarly, when animal 12 returns to a horizontal position, tether line 26 attached by means of a clamp 45 to animal 12 by collar 47 lowers causing counterbalanced arm 38 attached to tether 26 to rotate about pivot 68. This, in turn, causes the end of counterbalanced arm 38, as seen in FIG. 5, to rise, thereby passing through optical sensor 102 and interrupting the light emanating in direction of path 104. The passing of counterbalanced arm 38 through path 104 causes optical sensor 102 to be activated and to send a signal through its output lead 106 to computer 108. Computer 108 logs this activation as a second event.

As is well known to one skilled in the art, software or hardware residing in computer 108 is utilized to determine the number of vertical cycles of animal 12 by taking the number of logged events and dividing by two. Additionally, computer 108 includes a timer to log the time of an event to thereby subtract from the time that an initial event is logged, the time that a subsequent event is logged, to thereby determine the time animal 12 has spent in a vertical position.

Figure 6:
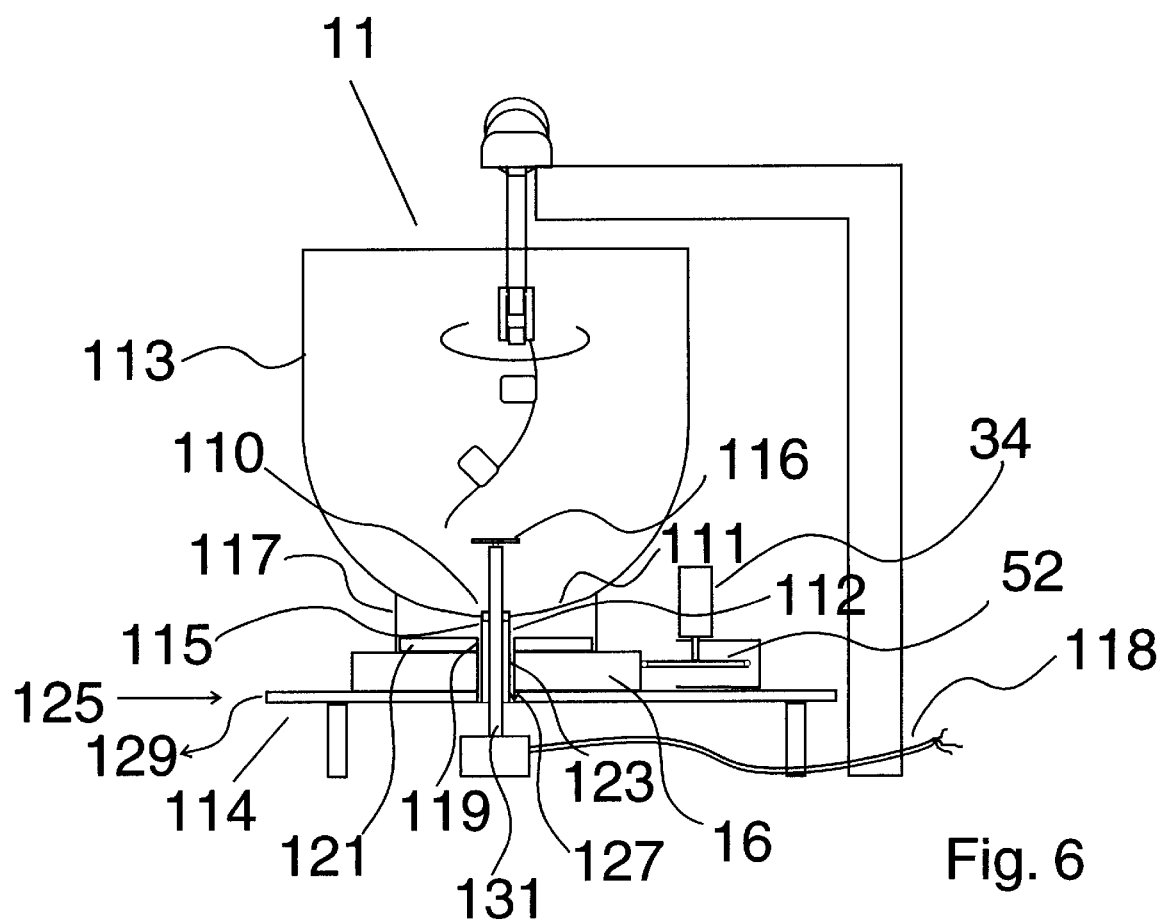
FIG. 6 shows a cross-sectional view of an embodiment of the apparatus including an operant behavior container.

Referring to FIG. 6, there is shown a cross-sectional view of an embodiment of system 11 including an operant behavior container. In the embodiment shown, hole 110 is located in bottom surface 111 of bowl 113. Hollow extension 112 is attached to bottom surface 111 of bowl 113 and aligned with hole 110 of bowl 113. Hole 115 is made in bowl base 117, hole 119 is made in plate 121, hole 123 is made in turntable 16, and hole 127 is made in support surface 129. Holes 115, 119, 123, and 127 are all aligned with each other and are sized such that hollow extension 112 fits within holes 115, 119, 123 and 127.

Support surface 129 is included in the embodiment of FIG. 6 and comprises the top portion of table 114 for support of rotating means 125 and bowl 113. In this embodiment, push bar 116, which serves as a means for determining operant behavior of animal 12, is placed within bowl 113, with aligned holes 110, 115, 119, 123, and 127 providing an access for supporting means 131 of push bar 116 located within bowl 113 as well as allowing signal wire 118 to be operatively connected to push bar 116. Thus, push bar 116 is supported within bowl 113 by supporting means 131.

Referring to FIG. 6, the operation of the system 11 in conducting operant behavior testing can be demonstrated. When animal 12 depresses push bar 116, a signal is sent to signal wire 118. As is well known to one skilled in the art, signal wire 118 may be connected to a recording or analytical device. Signal wire 118 may also be operatively connected to syringe pump 40 (see FIG. 1) such that when push bar 116 is depressed by animal 12, syringe pump 40 ejects a discreet amount of drug into lead 18 for delivery into animal 12.

Also within the scope of this invention are the use of other operant behavior devices including but not limited to omnidirectional levers, stimulus lights and foot shockers. It will be obvious to those acquainted with the art that bowl 113 is only exemplary of the type of container that can be used with system 11. Other containers, such as flat bottomed containers, are within the scope of the invention. Further, bowl base 117 and hollow extension 112, while adding some measure of stability to the embodiment disclosed, are not required in order to allow bowl 113 to be used as an operant chamber. Other applications of this invention will be obvious to those skilled in the art and are within the scope of this invention such as but not limited to the connection of an operant device to an electrical lead implanted in a specific region of the brain of animal 12 such that activation of the operant device produces or eliminates activation of the lead.

Figure 7:
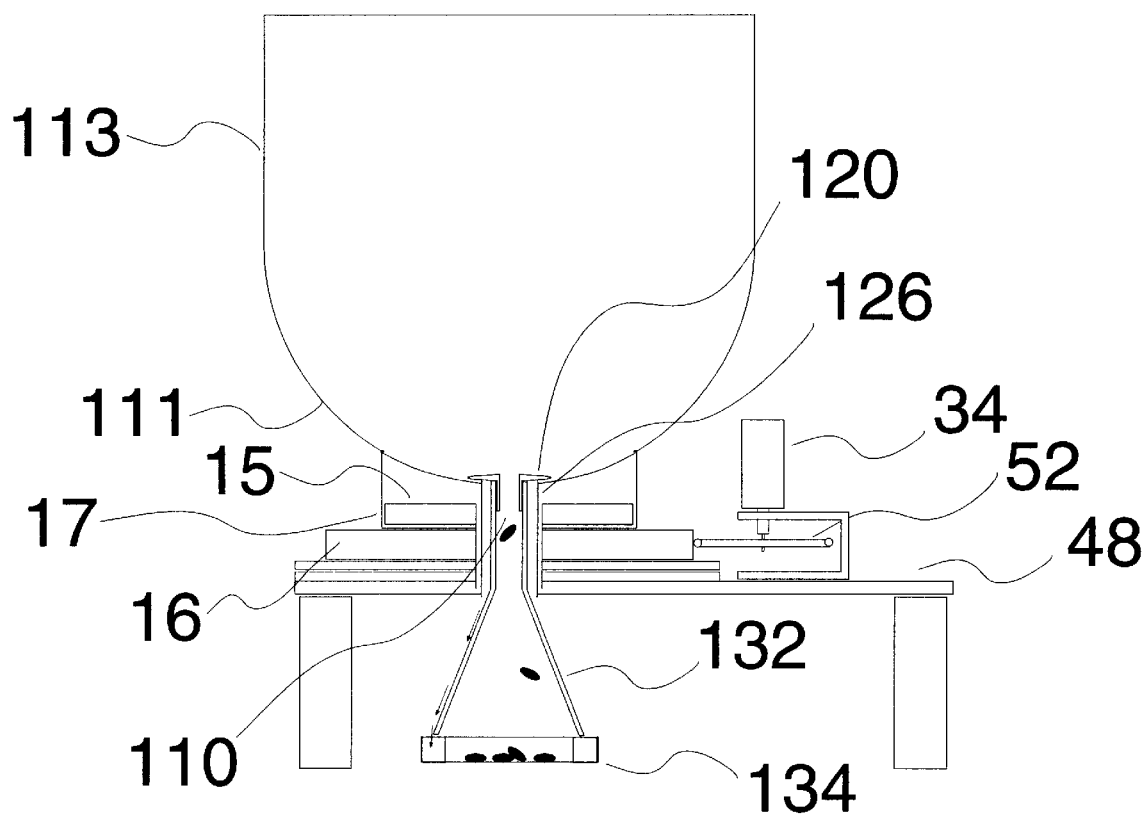
FIG. 7 shows a cross-sectional view of an embodiment of the apparatus including a metabolic container.

The apparatus of the present invention may also be used as a metabolic chamber. The embodiment of FIG. 7 shows bowl 113 which comprises a lower portion upwardly tapering from bottom surface 11. Also shown is stainless steel cap 120 placed within bowl 113 such that any urine or feces excreted by animal 12 will pass over cap 120. Stainless steel is chosen for its resistance to corrosion when exposed to urine as well as its hardness, since animal 12 may have a tendency to gnaw on cap 120.

Cap 120 is shown in greater detail in FIG. 8A and FIG. 8B. Specifically, in this embodiment cap 120 comprises a plurality of urine slots 122 sized such that urine will pass through urine slots 122 but which does not permit feces from animal 12 to pass through urine slots 122. Urine slots 122 are located around feces hole 124 which is sized such that feces from animal 12 will pass through. Hollow shaft 126 is attached to the lower surface of cap 120. Hollow shaft 126 serves the purpose of directing feces falling through feces hole 124 straight down. Pins 128 located on the lower surface of cap 120 are designed to fit within receptors 133 in bowl 113 (see FIG. 8C) providing for a more secure attachment of cap 120 to bowl 113.

The embodiment of cap 120 disclosed in FIG. 8A and FIG. 8B is circular, but other shapes are within the scope of the present invention. The salient feature of cap 120 is that it is sized to fit within bowl 113 in such a way that feces excreted by animal 12 will pass over the surface of cap 120, and not pass around the outside of cap 120 to hole 110 in the bottom of bowl 113. The shape and orientation of the disclosed embodiment is one of many shapes and orientations which are within the scope of this invention including but not limited to arcing slots following the circular contour of cap 120 and holes sized such that feces will not pass through. Also, although cap 120 is, in this embodiment, comprised of stainless steel, the present invention includes within its scope caps made from other materials possessing the desired properties of corrosion resistance and hardness.

Referring again to FIG. 7, funnel 132 is attached to hollow shaft 126 of cap 120 such that urine flowing through urine slots 122 is kept on the outer surface of funnel 132 while feces dropping through feces hole 124 stays inside of funnel 132. Collection dish 134 is aligned with hole 110 in bottom surface 111 of bowl 113 for collection of both the urine and feces. The manner in which urine and feces flow and are collected is described in greater detail below.

Figure 9A:
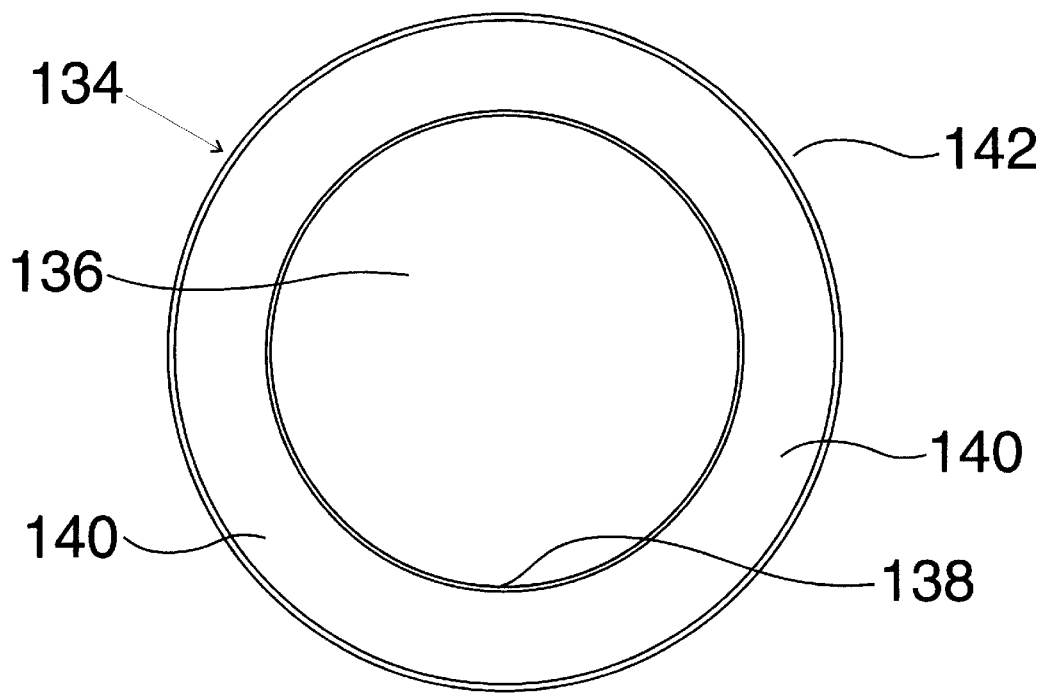
FIG. 9A and FIG. 9B show a top view and a side view, respectively, of one embodiment of the metabolic collection means of the present invention.
Figure 9B:
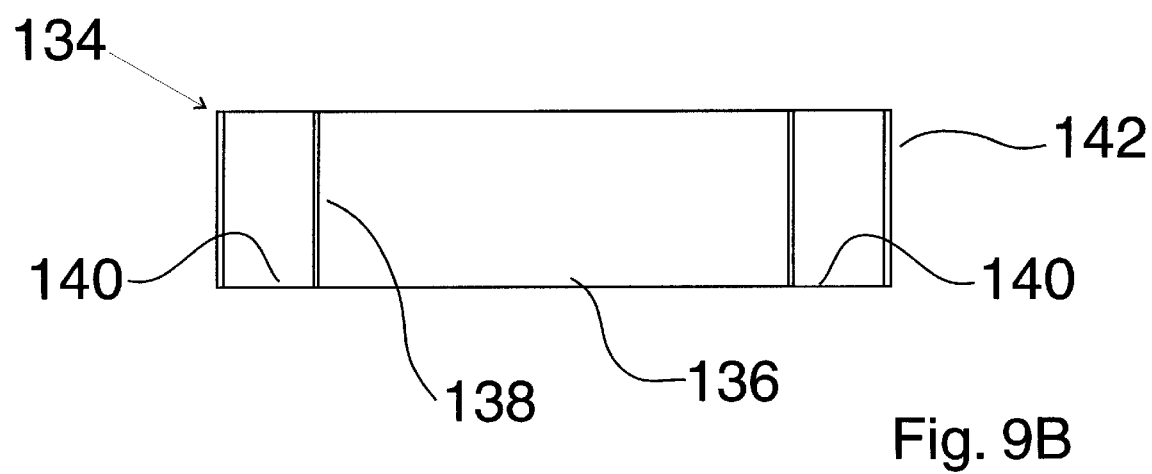

FIG. 9A and FIG. 9B show in greater detail metabolic collection dish 134. Collection dish 134 comprises inner compartment 136 defined by inner wall 138. Outer compartment 140 is defined by inner wall 138 and outer wall 142. When in position as shown in FIG. 7, inner compartment 136 is located underneath hole 110 in bottom surface 111 of bowl 113 and underneath hollow shaft 126 of cap 120. Inner compartment 136 is sized to be at least as large as hollow shaft 126 but not as large as flared end of funnel 132. Outer compartment 140 is sized such that entire collection dish 134 is larger than funnel 132, and larger than hollow extension 112. While the embodiment of FIG. 7 shows the flared end of funnel 132 to be larger than hollow extension 112, the scope of the invention includes but is not limited to a hollow cylinder with a slight outward taper at its lower end. The critical feature being the relative size and shape of compartments 136 and 140, hollow shaft 126, and the larger of hollow extension 112 or funnel 132. The combination of size and shape at a given cross-section is referred to as cross-sectional shape.

Referring again to FIG. 7, the operation of the metabolic chamber is described. As animal 12 passes feces, it is directed toward hole 110 in bottom surface 111 of bowl 113 by gravity. The feces hits the lower portion upwardly tapering from bottom surface 111 of bowl 113 and rolls to cap 120. The feces proceeds onto cap 120 and past urine slots 122. The feces does not pass through urine slots 122 since urine slots 122 are too small. The feces continues on to and through feces hole 124. Hollow shaft 126 and funnel 132 guide the feces into inner compartment 136 of collection dish 134.

When animal 12 passes urine, gravity directs urine toward hole 110 in bottom surface 111 of bowl 113. Urine contacts bowl 113 and flows down the lower portion upwardly tapering from bottom surface 111 of bowl 113 to cap 120. The urine proceeds over cap 120 to urine slots 122. The urine then passes through urine slots 122. The urine may free fall into outer compartment 140 of collection dish 134, or it may contact funnel 132 and run along the outside surface of funnel 132 to the bottom edge of funnel 132 where it falls into outer compartment 140 of collection dish 134. Some urine may pass through feces hole 124. If urine contacts hollow shaft 126, then it will flow along hollow shaft 126 to the outside surface of funnel 132, then flow down the outside surface of funnel 132 to the bottom edge of funnel 132 and drip into outer compartment 140 of collection dish 134. If urine passes through feces hole 124 and contacts funnel 132, the urine will flow down the interior surface of funnel 132 to the bottom edge of funnel 132 and drip into outer compartment 140 of collection dish 134. It is possible that a small amount of urine may pass through the feces hole 124 and not contact hollow shaft 126 or funnel 132. This small amount of urine will free fall into inner compartment 136 of collection dish 134.

The present invention includes within its scope cap 120 which allows urine to pass underneath cap 120. In this embodiment, cap 120 fits within bowl 113 such that urine may pass under cap 120 but feces can not pass under cap 120. In this embodiment, the flow path under cap 120 may be used in addition to urine slots 122 or in place of urine slots 122.

In the embodiment with no urine slots 122, the separation of urine from feces would occur as follows. As animal 12 passes feces, it is directed toward hole 110 in bottom surface 111 of bowl 113 by gravity. The feces hits the lower portion upwardly tapering from bottom surface 111 of bowl 113 and rolls to the cap 120. The feces does not pass under cap 120 since the gap between cap 120 and bottom surface 11 of bowl 113 is too small. The feces proceeds onto cap 120. The feces continues on to and through feces hole 124. Hollow shaft 126 and funnel 132 guide the feces into inner compartment 136 of collection dish 134.

When animal 12 passes urine, gravity directs urine toward hole 110 in bottom surface 111 of bowl 113. Urine contacts bowl 113 and flows down the lower portion upwardly tapering from bottom surface 111 of bowl 113 and underneath cap 120. The urine may free fall into outer compartment 140 of collection dish 134, or it may contact funnel 132 and run along the outside surface of funnel 132 to the bottom edge of funnel 132 where it will fall into outer compartment 140 of collection dish 134. Some urine may pass through feces hole 124. If urine contacts hollow shaft 126 then it will flow along hollow shaft 126 to the outside surface of funnel 132, then flow down the outside surface of funnel 132 to the bottom edge of funnel 132 and drip into outer compartment 140 of collection dish 134. If urine passes through feces hole 124 and contacts funnel 132, the urine will flow down the interior surface of funnel 132 to edge of funnel 132 and drip into outer compartment 140 of collection dish 134. It is possible that in this embodiment a small amount of urine may pass through the feces hole 124 and not contact hollow shaft 126 or funnel 132. This small amount of urine will free fall into inner compartment 136 of collection dish 134.

Figure 10:
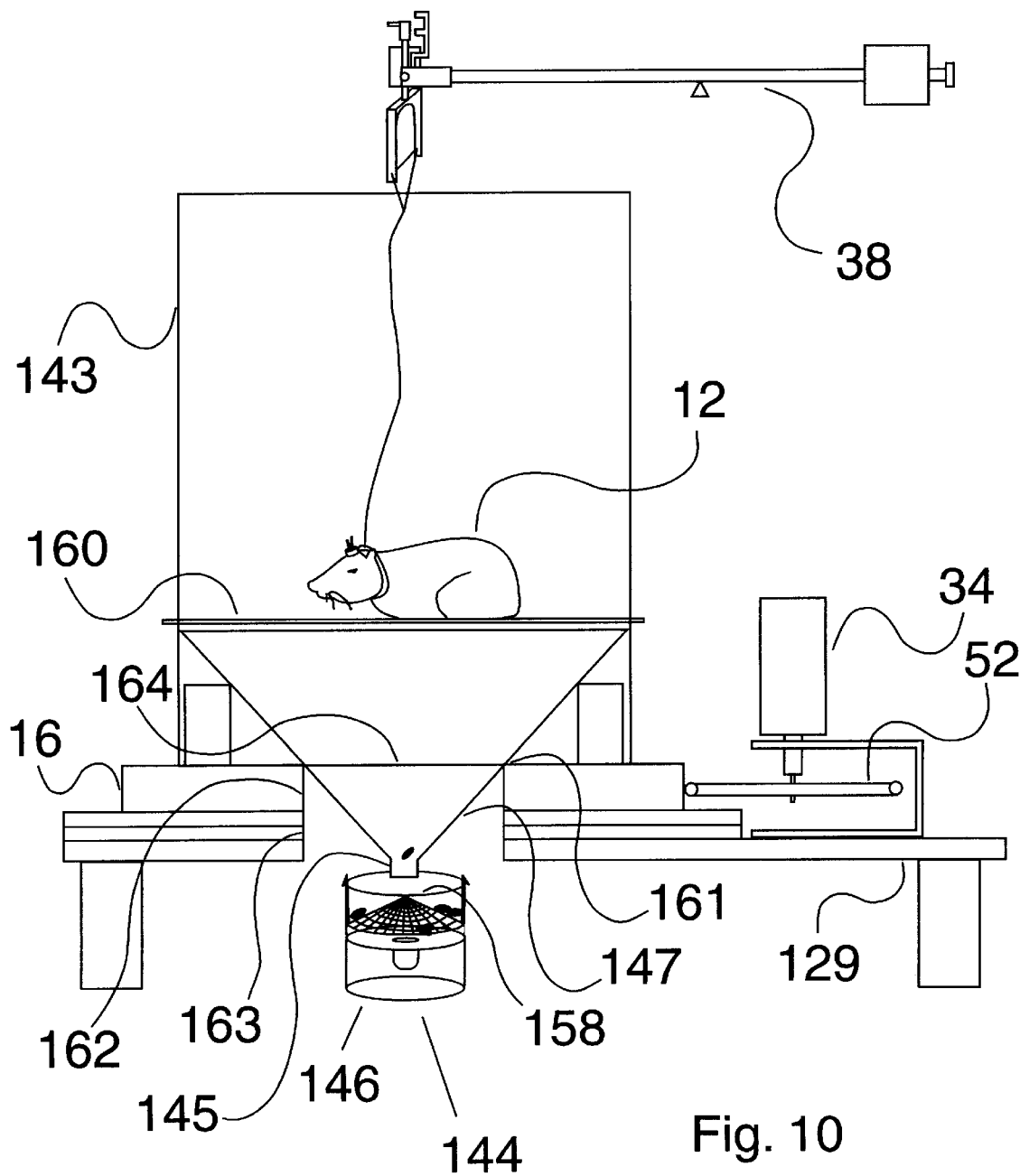
FIG. 10 shows a cross-sectional view of an embodiment of the apparatus including an alternative metabolic container.

An alternate embodiment of a metabolic cage is shown in FIG. 10. In this embodiment, means for separating the feces from the urine 146 is external to bowl 143, which in this embodiment comprises a cylindrically-shaped container. Positioned above bottom surface 164 of bowl 143 is animal support means 160. Animal support means 160 comprises, in this embodiment, a plurality of overlapping members, which comprise apertures of a size to allow feces and urine to pass through. As is well known in the art, the members may be wire, such as in a wire mesh, or rods, such as in a grid. Those skilled in the art will be aware of alternative embodiments of animal support means to 160, which are within the scope of the present invention, which includes but is not limited to, a plurality of substantially parallel members such as rods. Apertures 161, 162, and 163 are formed within bottom surface 164 of bowl 143, turntable 16, and bowl support surface 129, respectively, for receipt of funnel 147 therethrough as illustrated. Funnel 147 rotates with bowl 143 in this embodiment, but is not required to so rotate unless animal support means 160 is attached to funnel 132 instead of the walls of bowl 143.

Funnel 147 extends below the underside of bowl support surface 129 and includes hole 145. Hole 145 of funnel 147 is positioned over alternate collection dish 144 as shown. Alternate collection dish 144, which is shown in greater detail in FIG. 11, collects urine and feces excreted by animal 12 in the manner which is described in further detail herein.

Figure 11:
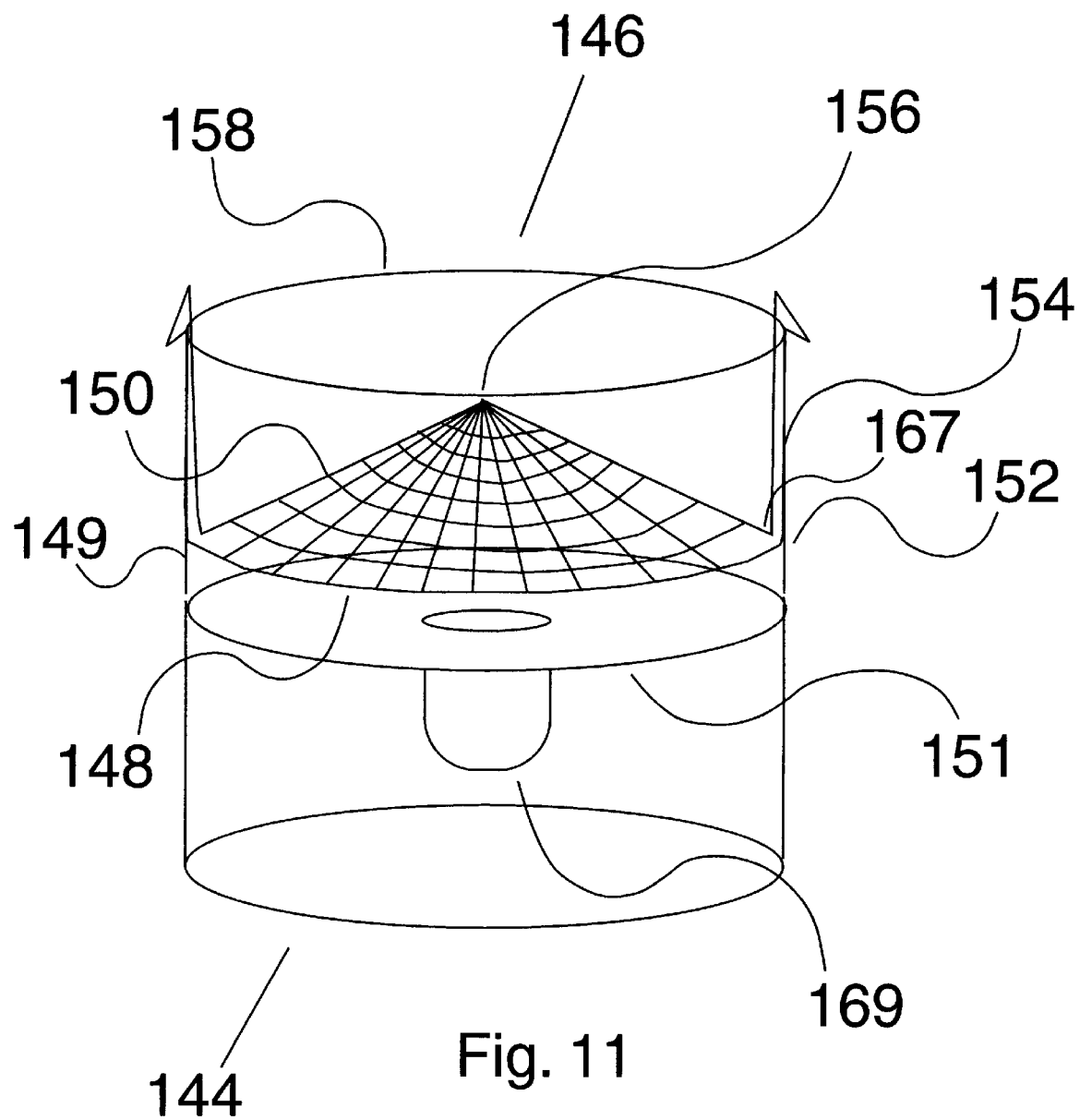
FIG. 11 shows a cross-sectional view of an alternative means for separating the feces from the urine.

FIG. 11 shows a cross-sectional view of means for separating feces and urine 146 and collection dish 144 utilized in the embodiment of FIG. 10. As illustrated, positioned within collection dish 144 is means for separating feces and urine 146, comprising mesh 148. Mesh 148 is formed into tapered section 150 which descends to lower rim 152. Mesh 148 is of the type that urine will pass through but that feces will not pass through and comprises a stainless steel mesh, or may be made of other materials which resist corrosion. Vertical section 154 of mesh 148 extends upward from lower rim 152 of mesh 148. In this embodiment, mesh 148 is positioned within collection dish 144 due to the fact that mesh 148 is formed to have its lower rim 152 and vertical section 154 in frictional contact with the interior of side wall 149 of collection dish 144, and such that apex 156 of mesh 148 is lower than upper rim 158 of collection dish 144, and such that lower rim 152 of mesh 148 is held above bottom surface 151 of collection dish 144. Depression 169 is provided in bottom surface 151 of collection dish 144 to concentrate urine.

Referring now to FIG. 10, the operation of the alternate metabolic cage is explained. After being excreted by animal 12, both feces and urine fall through the apertures of animal support means 160, and are then directed by gravity into funnel 147. Feces and urine then roll and flow, respectively, through hole 145 of funnel 147. Passing through hole 145, feces and urine fall past upper rim 158 of collection dish 144. Both feces and urine then hit at or about apex 156 or tapered section 150 of mesh 148. Urine will then pass through mesh 148, and fall into collection dish 144. Urine flows along bottom surface 151 of collection dish 144 to depression 169 where urine is concentrated. Feces, being too large to pass through mesh 148, is directed by tapered section 150 of mesh 148 to gully 167 formed at the junction of vertical section 154, and tapered section 150 of mesh 148. While in gully 167, the feces is out of the direct path of any urine which may be later excreted by animal 12.

The embodiment of the combination of mesh 148 and alternate collection dish 144 is one of many embodiments within the scope of the present invention. Mesh 148 may be comprised of any material or structure which will allow urine therethrough while not permitting feces to pass therethrough, such as, but not limited to, the use of a formed grid or a netting over a form. Further, the method of suspending mesh 148 above bottom surface 151 of collection dish 144 may be a rack or stand as opposed to friction. Additionally, collection dish 144 may be of the type shown in FIG. 9A and FIG. 9B, with mesh 148 covering inner compartment 136, allowing feces to collect in outer compartment 140. Further, use of funnel 147 is but one embodiment which is within the scope of the present invention. Other embodiments such as bowl 113 (see FIG. 7) are within the scope of the present invention. Several other embodiments of this invention will be obvious to persons skilled in the art, said embodiments falling within the scope of the present invention.

Figure 12:
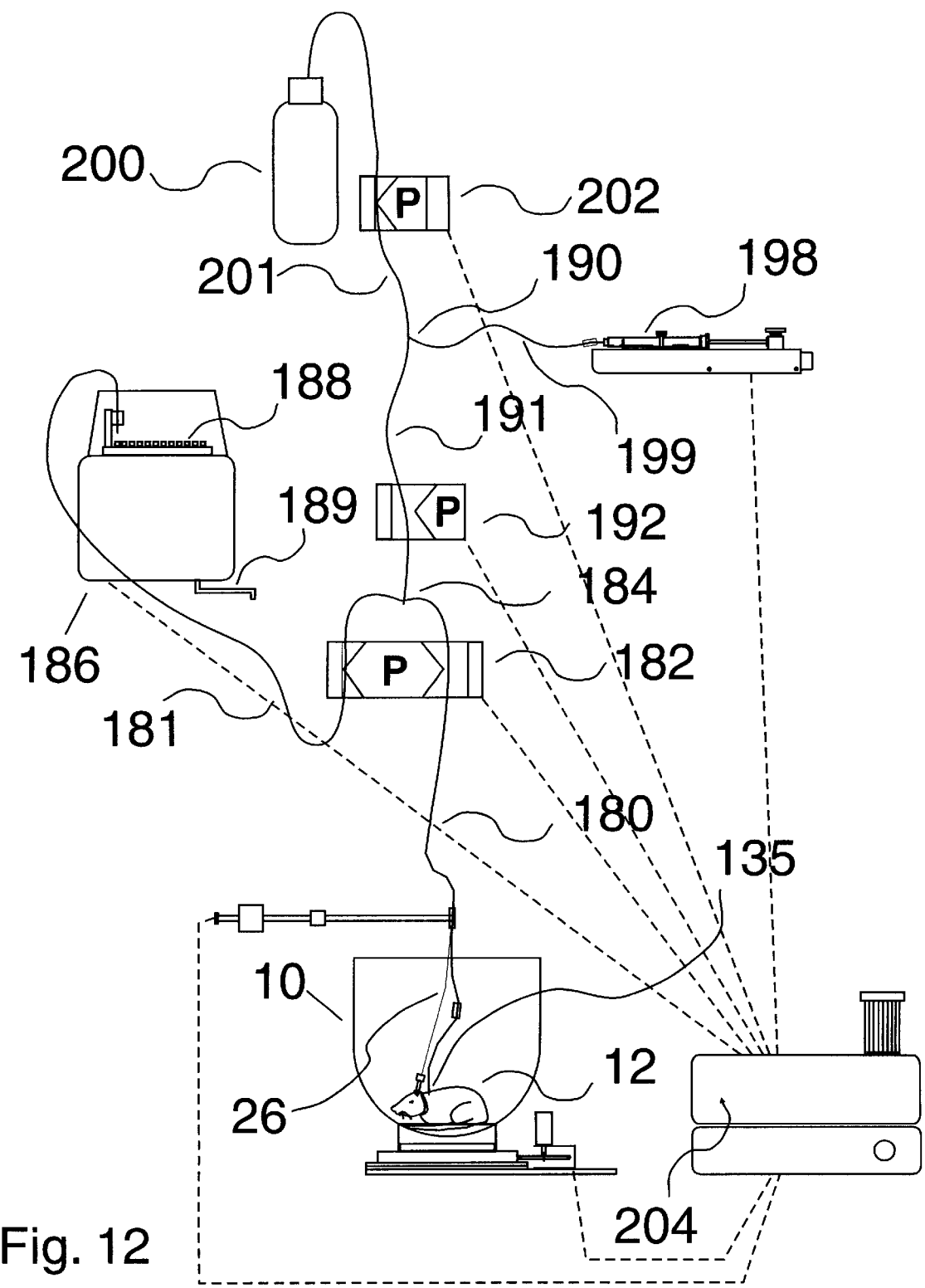
FIG. 12 shows a diagramatic view of one embodiment of the apparatus for automated micro sampling of blood according to the present invention.

An apparatus for performing automated micro blood sampling in animals is diagramed in FIG. 12. In this embodiment, animal 12 is placed within movement-responsive system of the type shown in FIG. 1. Attached to animal 12 is tether 26, and a jugular cannula having sterile heparinized catheter 135 attached thereto for removal of blood from animal 12. Catheter 135 is connected to lead 180, by utilizing short polymeric tubes which provide a secure connection by sliding over the ends of the two pieces of tubing being connected. Such an additional connector may result in clotting or leaking of blood passing through the connector. Further, test lead 180 comprises, in this embodiment, tubing having an anti-coagulant coating in the inside thereof to resist clotting within test lead 180. Such anti-coagulant coating may be Carmeda® Bioactive Surface (CBAS), available from Carmeda, of Stockholm, Sweden.

Test lead 180 is routed through three-way pinch valve 182 to first intersection or "T" 184, where test lead 180 is joined with collector tubing 181 and connector tubing 191. Collector tubing 181 extends from first "T" 184 through three-way pinch valve 182 to refrigerated fraction collector 186. Fraction collector 186 includes sealed vials 188 for receiving blood samples and drain 189, all as is well known in the art. The present invention includes within its scope sample collection means other than refrigerated fraction collectors. It will be obvious to those skilled in the art that for performance of some experiments, the sample collection means will not need a drain, and the saline and sample may be intermixed.

Three-way pinch valve 182 through which test lead 180 and collector tubing 181 extend is of a type well known in the art, and may comprise, for example, Model 161P, manufactured by NR Research of Caldwell, N.J. Other means for stopping or allowing fluid flow through tubes 181 and 180 will be obvious to those skilled in the art and are considered to be within the scope of the present invention. During operation of three-way pinch valve 182 either test lead 180 or collector tubing 181 is open with the other closed. Test lead 180 and collector tubing 181 cannot both be open or both be closed by operation of three-way pinch valve 182.

Connector tubing 191 extends from first "T" 184 through second pinch valve 192 to second intersection or "T" 190. Other means for controlling fluid flow through tube 191 will be obvious to those skilled in the art and are considered to be within the scope of the present invention. Also extending from second "T" 190 is syringe tubing 199 which is, in turn, connected to syringe pump 198. Syringe pump 198 is of the type that can be controlled to force fluid into or withdraw fluid from syringe tubing 199, and may comprise, for example, a modified Model Baby Bee, manufactured by Bioanalytical Systems, Inc. of West Lafayette, Ind. It will be obvious to those skilled in the art that other means for moving fluid can be substituted for syringe pump 198 and are considered within the scope of this invention. Other means for moving fluid include but are not limited to a reciprocal piston pump, peristaltic pump, or any other vacuum/pressure source.

Reservoir tubing 201 also extends from second "T" 190, goes through third pinch valve 202 and is connected to sterile saline reservoir 200. Sterile saline may be housed within saline reservoir 200. In the present embodiment, as will be discussed later, blood is not drawn into reservoir tubing 201; therefore, there is no concern for clotting due to contact of blood in the means for controlling fluid flow through reservoir tubing 201. It will be obvious to those skilled in the art that a wide variety of fluid control means can be used in place of third pinch valve 202. It will be further obvious to those skilled in the art that it is not necessary to have sterile saline reservoir 200 in the apparatus for performing automated micro blood sampling. For example, in another embodiment, syringe pump 198 is connected to syringe tubing 199 which is in turn connected to first "T" 184. In this embodiment, second "T" 190, connector tubing 191, and third pinch valve 202 are omitted, and second pinch valve 192 may be located so as to control the flow of fluid through syringe tubing 199, or may be omitted.

In the embodiment of FIG. 12, certain components, namely, test lead 180, collector tubing 181, connector tubing 191, and first "T" 184, all have an anti-coagulant coating, such as CBAS, in the inside thereof to prevent clotting of blood within these devices. Because, as discussed later herein, no blood will flow within second "T" 190, and syringe tubing 199, they may, but need not, be made from plain tubing or material, i.e., tubing or material without an anti-coagulant coating in the inside thereof. First and second "T"s 184 and 190 may comprise separate tubing connectors for connection to three tubes. "T" 184 must also include an anti-coagulant coating therein. In the alternative, first and second "T"s 184 and 190 may simply comprise the point at which the tubes are joined by means well known in the art and without the use of a separate connector.

Second and third pinch valves 192 and 202, respectively, are intended for use with only a single tube—to open or close that tube—and may comprise, for example, Model 161P, manufactured by NR Research of Caldwell, N.J.

The blood sampling system of FIG. 12 also includes controller 204 for automated control of the system as is described in greater detail herein. Controller 204, which comprises, in this embodiment, a computer and software, is operatively connected, by means well know in the art to: (a) three-way pinch valve 182; (b) second pinch valve 192; (c) third pinch valve 202; (d) syringe pump 198; (e) fraction collector 186; and (f) movement-responsive system 10. By the operable connection of controller 204 to movement-responsive system 10, the behavior of animal 12 may be monitored and analyzed, as described earlier herein, and other test leads that may be connected to animal 12 can be controlled. In another embodiment, the movement responsive system is independent of controller 204 and uses a separate controller. By its other operable connections, controller 204 can control the positions of three-way pinch valve 182 to cause the alternate opening and closing of test lead 180 and collector tubing 181; control the open and closed positions of second and third pinch valves 192 and 202, respectively, to cause the opening and closing of connector tubing 191 and reservoir tubing 201, respectively; control syringe pump 198 for forcing fluid into or withdrawing fluid from syringe tubing 199; and control fraction collector 186 to either receive blood samples into the vials 188 or pass fluid coming from collector tubing 181 into drain 189.

The present invention may be used to sample body fluids other than blood, either separately or in combination with blood sampling and other biomedical testing. Bile, for example, may be sampled using the present invention. Bile salts are added to the wash fluid for replacement of salts removed in the sampling process, thereby avoiding any imbalances due to removal of the bile salts. The combination of bile and blood sampling allows for a complete picture of drug metabolism. Other applications will be obvious to those skilled in the art and are within the scope of the present invention.

Figure 13:
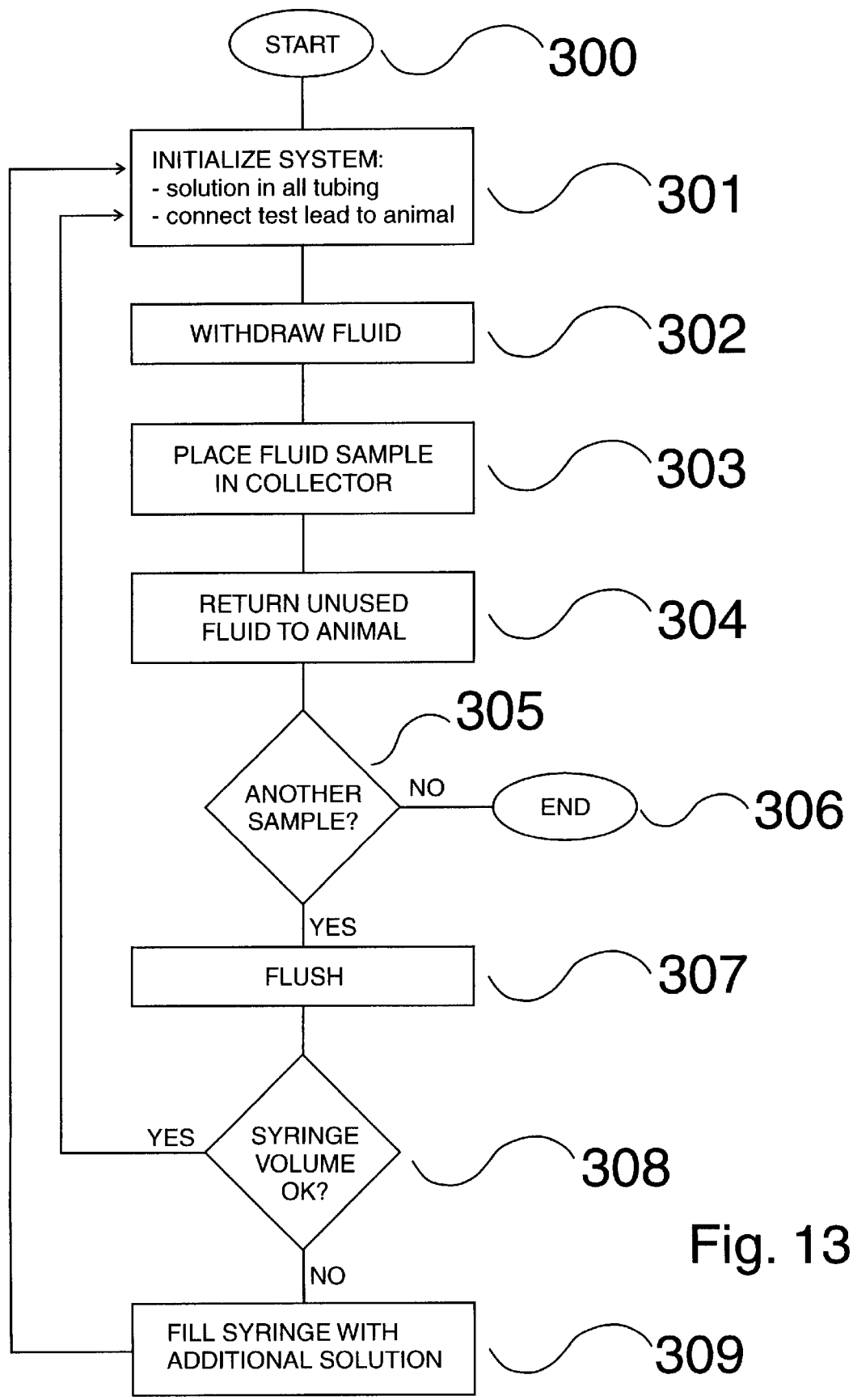
FIG. 13 shows a flowchart of a method for conducting automated micro sampling of blood.

Operation of the apparatus for conducting automated micro blood sampling is explained by referring to FIG. 12 and to FIG. 13, which is a flow chart of the following operations. When an operator decides, at step 300, to take one or more blood samples from animal 12, the blood sampling system according to the present invention must first be initialized. As set forth in step 301, initialization of the system is accomplished by filling all tubing with sterile saline and by connecting test lead 180 to animal 12.

Test lead 180, collector tubing 181, connector tubing 191, syringe tubing 199, and reservoir tubing 201 are all filled with sterile saline solution residing in reservoir 200 according to the following steps:

(a) Second pinch valve 192 is placed in the closed position and third pinch valve 202 is placed in the open position.

(b) Syringe pump 198 is controlled to withdraw a predetermined amount of saline from reservoir 200. The predetermined amount must be at least as great as the volume of the blood sample to be collected, plus the total volume of test lead 180, twice the volume of collector tubing 181, connector tubing 191, syringe tubing 199, and reservoir tubing 201, plus the volume of first and second "T"s 184 and 190, respectively, if first and second "T"s 184 and 190 introduce additional volume as would be the case if first and second "T"s comprise separate connectors, and the volume of any desired flush (as described at step 307 below).

(c) Third pinch valve 202 is then closed.

(d) Second pinch valve 192 is opened.

(e) Control syringe pump 198 to force saline of an amount equal to the volume of connector tubing 191 plus either the volume of collector tubing 181 between fraction collector 186 and connector 184, and the volume of 184, if three-way pinch valve 182 is positioned to cause test lead 180 to be closed, or the volume of test lead 180 between catheter 135 and connector 184, and the volume of connector 184, if three-way pinch valve 182 is positioned to cause collector tubing 181 to be closed.

(f) Alternate the position of three-way pinch valve 182.

(g) Control syringe pump 198 to force saline of an amount equal to either the volume of collector tubing 181 between fraction collector 186 and connector 184 if three-way pinch valve is positioned to cause test lead 180 to be closed, or the volume of test lead 180 between catheter 135 and connector 184 if three-way pinch valve 182 is positioned to cause collector tubing 181 to be closed.

Next, in step 302, blood of an amount sufficient to produce a blood sample is withdrawn from animal 12. To withdraw blood, three-way pinch valve 182 must be positioned to close connector tubing 181 and open test lead 180. Then, syringe pump 198 is controlled to withdraw saline of a volume equal to the volume of test lead 180 and first "T" 184 plus an amount equal to the volume of the desired blood sample. This results in test lead 180 and connector 184 being filled with blood and blood of the amount of the desired blood sample to be located in connector tubing 191.

To place the withdrawn blood sample volume into fraction collector 186, indicated as step 303, the following steps are then taken:

(a) The position of three-way pinch valve 182 is alternated so that test lead 180 is closed and collector tubing 181 is open.

(b) Fraction collector 186 is controlled so that fluid goes to drain 189.

(c) Syringe pump 198 is controlled to introduce saline of a volume equal to the volume of collector tubing 181 between first "T" 184 and fraction collector 186. This moves the blood sample into collector tubing 181 and to the end of collector tubing 181 nearest fraction collector 186.

(d) Fraction collector 186 is controlled so that fluid passes to one of vials 188.

(e) Syringe pump 198 is controlled to introduce saline of a volume equal to the volume of the blood sample, thereby forcing the blood sample into one of vials 188.

The unused withdrawn blood is then returned to animal 12 in step 304. Specifically, three-way pinch valve 182 is positioned so that test lead 180 is open and collector tubing 181 is closed. Syringe pump 198 then introduces saline of a volume equal to the volume of blood initially withdrawn from animal 12. This has the effect of returning all unused blood within test lead 180 plus a volume of saline equal to the volume of the blood sample collected to animal 12. In this manner, animal 12 will not become dehydrated as a result of the blood sampling tests performed. Three-way pinch valve 182 is then alternated so that test lead 180 is closed and collector tubing 181 is open.

If, at step 305, it is determined that no additional blood samples are necessary or desired, the method of blood sampling ends at step 306. If, on the other hand, additional blood samples are necessary or desired, in step 307 a flush is performed. Specifically, control fraction collector 186 so that fluid passes to drain 189 and control syringe pump 198 to introduce saline of a volume equal to the volume of the blood sample collected in step 303 plus the volume of connector 184 and collector tubing 181, thereby flushing the part of connector tubing 191 which was exposed to blood in step 302, connector 184, and collector tubing 181.

At step 308 it is determined whether syringe pump 198 has a sufficient volume of sterile saline available to perform another blood test. If enough saline is available, the method returns to step 302 to withdraw additional blood. If insufficient saline is available, syringe pump 198 is filled with additional saline at step 309.

To place additional saline in syringe pump 198, second pinch valve 192 is closed and third pinch valve 202 is opened. Syringe pump 198 then withdraws saline from reservoir 200. Finally, before returning to step 302 to withdraw additional blood, third pinch valve 202 is closed and second pinch valve 192 is opened.

It will be appreciated by those of skill in the art that, with the exception of connecting catheter 135 to test lead 180, all of the above steps (300–309) may be controlled by controller 204 to result in an automated blood sampling method. To do so, controller 204 must be able to send control signals to three-way pinch valve 182, second pinch valve 192, third pinch valve 202, syringe pump 198, and fraction collector 186, all of which are operably connected to controller 204. In one embodiment, controller 204 receives a signal from syringe pump 198 indicative of the saline volume in syringe pump 198 to ensure proper volumes of saline are pumped and withdrawn, and/or are available for obtaining the next blood sample.

It will be appreciated by those skilled in the art that the above apparatus and method for automated micro sampling of blood is a significant improvement over the prior art. The use of anti-coagulant coated tubing and "T"s significantly reduces the possibility of blood clotting within the system. The absence of liquid swivels not only reduces risk of leakage and clotting, but allows for smaller amounts of blood to be withdrawn from animal 12 for samples. The taking of smaller blood samples is a benefit to animal 12, and also reduces the time required to effect the sample. Further, the use of syringe pump 198 increases the control over fluid, reducing the error volume associated with automated sampling. The use of pinch valves, which do not physically contact the blood, further reduces the potential for clotting and leaks in the system. The apparatus also uses non-heparinized sterile saline solution to allow blood serum sampling to be performed on blood samples withdrawn from animal 12. All of these benefits are provided with an apparatus which is inexpensive, easy to setup, and easy to maintain, and with a method that is easy to perform in a time efficient, reliable manner.

It will also be appreciated by those of skill in the art that the movement-responsive system of the present invention provides for the use of continuous leads (tubing, electric lines and optic fibers) without the use of swivels or commutators. This provides for numerous advantages over the prior art including, but not limited to: (a) elimination of the need to compensate for and accommodate the extra system volume of a liquid swivel; (b) no restrictions of the number and type of electrical, fluid or optical leads used in testing; (c) no restrictions on the relative placement of different types of leads; (d) elimination of the need to compensate for the liquid travel time when a swivel is employed; (e) no cross-contamination between channels of a multi-channel liquid swivel; (f) elimination of the potential for cross-talk between electrical or optical channels on a commutator and noise or interference caused by a commutator; (g) avoidance of the extra expense resulting from continual replacement or repair of swivels seals or commutators which experience wear during normal use; (h) elimination of the potential of blood clotting within the liquid swivel; and (i) elimination of the difficulties associated with sterilization when aseptic connections are required.

It will also be appreciated that the present invention provides for tracking and analysis of the rotational and vertical behavior of the animal. Such tracking and/or analysis provides general indicators of the activity of the subject animal and specific indicators of neurochemical or metabolic changes that may be occurring in the animal during testing, and therefore can be very valuable to a researcher.

It will be further appreciated that the present invention provides an apparatus whereby no unwanted stress is placed on the test lead. In some prior art systems, an actual lead is used to move a physical portion of the apparatus which places stress on the lead, and which can harm the animal or result in disconnection of the lead from the animal or to the external device to which the lead is connected.

It will also be appreciated by those of skill in the art that the use of close-ended limit detectors means that counterrotation of the cage in response to rotation of the animal may be invoked in sufficient time to avoid entanglement, twisting, disconnection or clamping of the leads as results in prior art systems using open-ended sensors which may require one or more revolutions of the animal before reacting with counter-rotation.

Further, it will be appreciated that the present invention provides the researcher with a great deal of flexibility in the types of tests that can be performed with the apparatus. The researcher is not limited to a specific type of lead or leads or a specific number of leads. All this is accomplished with a system which is inexpensive to manufacture, repair and maintain, and which is also highly reliable during operation.

It will be further appreciated that the present invention provides the researcher with the added flexibility of performing operant behavior and metabolic testing in a system which is not limited to a specific number or type of leads, and which does not require the use of swivel commutators or commutators.

It will also be appreciated that the current invention provides a method and apparatus for automated method for micro sampling of blood which is inexpensive, provides precise sampling capability with a high degree of repeatability, significantly reduces the potential for clotting, allows for blood serum sampling, and is easier to set up and maintain than prior art systems.

As used herein and in the claims, "biomedical test" includes, but is not limited to, infusion, electrophysiology blood monitoring, microdialysis, ultrafiltration, electrochemistry, optical fiber transmission, blood sampling, and behavior monitoring. Essentially, it is any test that may be performed on freely-moving animal in a laboratory environment which requires the use of one or more "leads". A "lead" includes fluid tubing, electrical line, optic fiber or other line which is connected to the animal at one end and to an external device at its other end for the purpose of transmission of fluids, light or other stimuli or transmission/receipt of electrical signals, fluids, light transmissions from devices within or on the animal or other data from within or on the animal. The "external device" to which a "lead" is connected at its other end may comprise a source, such as a source of fluid or other stimuli, or a device capable or receiving response signals, fluids, or data from the animal.

Also, as used herein and in the claims, "limit detector" means a close-ended sensor which is activated by means such as interruption or reflection of a light beam, magnetic field, radiation field, a flow of air or liquid, or a simple contact with a microswitch, pressure sensitive button, magnet, electrical contact wire, or other mechanism. The "triggering element" may comprise the rotatable element disclosed in the Figures, or any other means of triggering such a limit detector in accordance with the limit detector's activation mechanism and in response to rotational movement of the animal. The angle or spacing between the limit detectors is determined by the angle between or the spacing between (for a non-rotational triggering element) the "primary sensing axis" of the limit detectors, such as the positional axis of optical sensors 70 and 72, as measured in relation to the type of triggering element, i.e., rotational, linear, etc. Thus, in respect to the type of movement of triggering element, the limit detectors are in a predetermined relative position with respect to each other. The limit detectors are thus "logically" connected to the rotating means by electrical, physical, magnetic or light contacts to cause activation and deactivation of the rotation of the cage in response to movement (rotational, or otherwise) of the triggering element.

What is claimed is:

1. An apparatus for performing at least one biomedical test on a freely-moving animal, comprising:
   a container for housing the animal, the container comprising a bottom surface having a hole therethrough;
   means for rotating the container, the rotating means operably connected to the container, the rotating means comprising a hole positioned such that when the container is placed on the rotating means, the hole of the rotating means aligns with the hole in the bottom surface of the containers;
   means for sensing rotational movement of the animal, the sensing means including
      first and second activatable limit detectors having a primary sensing axis, the first and second limit detectors positioned such that the primary sensing axes of the limit detectors are at a predetermined relative position with respect to each other, the first and second limit detectors logically connected to the rotating means to cause clockwise and counterclockwise movement, respectively, of the rotating means upon activation thereof, and
      a moveable triggering element having at least a portion thereof for activation and deactivation of the first and second limit detectors;
   means for supporting the sensing means above the animal, the support means connected to the sensing means; and
   means for tethering the animal to the sensing means, the tether means having first and second ends, the first end for connection to the animal, and the second end connected to the triggering element of the sensing means,
   such that rotational movement of the animal causes movement of the tether means which in turn causes movement of the triggering element of the sensing means, and upon activation of either the first or second limit detectors by the portion of the triggering element for activation of the first and second limit detectors results in counter-rotation of the container by the rotating means by activation of the respective limit detector.

2. The apparatus of claim 1, further comprising means for determining operant behavior of the animal housed within the container, the means for determining operant behavior including support means for supporting the means for determining operant behavior within the container, the support means passing through the hole of the bottom surface of the container and the hole of the rotating means when the container is placed on the rotating means.

3. The apparatus of claim 2, wherein the means for determining operant behavior comprises a push bar.

4. The apparatus of claim 1, wherein the container is upwardly tapered from the bottom surface, such that urine and feces excreted from the animal is gravity-fed toward the hole in the bottom surface of the container, the apparatus further comprising;
   means for separating the feces from the urine aligned with the hole in the bottom surface of the container and the hole of the rotating means and proximate the hole in the bottom surface of the container and the hole of the rotating means.

5. The apparatus of claim 4, further comprising a hollow extension connected to the bottom surface of the container and aligned with the hole in the bottom surface of the container, and wherein the means for separating the feces from the urine comprises:
   a plate having a lower and an upper surface, the plate having at least one hole therethrough sized so as to pass feces, the plate having at least one aperture therethrough sized such that urine will pass through but feces will not pass through;

a hollow shaft attached to the lower surface of the plate; and a hollow funnel having a neck portion and a flared portion, the neck portion sized such that it can be attached to the hollow shaft attached to the lower surface of the plate, such that when the neck portion of the funnel is attached to the hollow shaft, urine is permitted to flow through the at least one aperture in the plate, between the hollow extension and the hollow shaft, and be guided downward by the flanged portion of the funnel, and such that feces is permitted to fall through the at least one hole in the plate and through the hollow shaft.

6. The apparatus of claim 5, further comprising:

collection means for collecting fluids, the collection means having a bottom surface, an outer wall and an inner wall, the collection means at the outer wall larger than the flared portion of the funnel and larger than the hollow extension, the collection means at the inner wall smaller than the flared portion of the funnel and not smaller than the hollow shaft, the collection means aligned with the hollow shaft and proximate to the flared portion of the funnel, the collection means located underneath the hollow shaft and underneath the flared portion of the funnel, such that urine guided by the flared portion of the funnel falls into the collection means between the inner and outer wall, and such that feces falling through the hollow shaft will fall into the collection means within the inner wall.

7. The apparatus of claim 4, further comprising a hollow extension connected to the bottom surface of the container and aligned with the hole in the bottom surface of the container, wherein the means for separating the feces and the urine comprises:

a tapered section, a lower rim, and an apex, the lower rim of the means for separating being larger than the hollow extension, the means for separating being permeable and sized to allow urine to pass through the means but to prohibit feces from passing through the means for separating.

8. The apparatus of claim 7, further comprising urine collection means having a bottom surface and at least one wall, the urine collection means being larger than the hollow extension and not larger than the means for separating, the collection means being aligned with the means for separating and located underneath the means for separating.

9. The apparatus of claim 8, wherein the at least one wall of the urine collection means has an upper rim, and wherein the separating means is located within the urine collection means, further comprising:

means for supporting the separating means such that the apex of the separating means is maintained in a position lower than the upper rim of the wall of the urine collection means, and such that the lower rim of the separation means is above the bottom surface of the collection means.

10. The apparatus of claim 9, wherein the means for supporting the separating means comprises the lower rim of the separating means sized for frictional contact with the wall of the urine collection means.

11. The apparatus of claim 7, further comprising feces collecting means for receiving feces positioned proximate the separating means such that feces falling on the separating means will be directed to the feces collecting means.

12. The apparatus of claim 11, wherein the separating means further comprises a vertical portion circumscribing the lower rim and extending upward from the lower rim, and wherein the feces collecting means comprises;

a gully formed by the vertical portion of the insert and the tapered section of the insert.

13. An apparatus for performing at least one biomedical test on a freely-moving animal, comprising:

a container for housing the animal;

means for rotating the container, the rotating means operably connected to the container;

means for sensing rotational movement of the animal, the sensing means including first and second activatable limit detectors having a primary sensing axis, the first and second limit detectors positioned such that the primary sensing axes of the limit detectors are at a predetermined relative position with respect to each other, the first and second limit detectors logically connected to the rotating means to cause clockwise and counterclockwise movement, respectively, of the rotating means upon activation thereof, and a moveable triggering element having at least a portion thereof for activation and deactivation of the first and second limit detectors;

means for supporting the sensing means above the animal, the support means connected to the sensing means;

means for tethering the animal to the sensing means, the tether means having first and second ends, the first end for connection to the animal, and the second end connected to the triggering element of the sensing means, such that rotational movement of the animal causes movement of the tether means which in turn causes movement of the triggering element of the sensing means, and upon activation of either the first or second limit detectors by the portion of the triggering element for activation of the first and second limit detectors results in counter-rotation of the container by the rotating means by activation of the respective limit detector; and means for supporting the animal above the bottom surface of the container.

14. The apparatus of claim 13, wherein the means for supporting the animal comprises a plurality of overlapping members.

15. The apparatus of claim 13, wherein the means for supporting the animal comprises a plurality of substantially parallel members.

16. An apparatus for performing at least one biomedical test on a freely-moving animal, comprising:

a container for housing the animal;

means for rotating the container the rotating means operably connected to the container;

means for sensing rotational movement of the animal, the sensing means including first and second activatable limit detectors having a primary sensing axis, the first and second limit detectors positioned such that the primary sensing axes of the limit detectors are at a predetermined relative position with respect to each other, the first and second limit detectors logically connected to the rotating means to cause clockwise and counterclockwise movement, respectively, of the rotating means upon activation thereof, and a moveable triggering element having at least a portion thereof for activation and deactivation of the first and second limit detectors;

means for supporting the sensing means above the animal, the support means connected to the sensing means;

means for tethering the animal to the sensing means, the tether means having first and second ends, the first end for connection to the animal, and the second end connected to the triggering element of the sensing means, such that rotational movement of the animal causes movement of the tether means which in turn causes movement of the triggering element of the sensing means, and upon activation of either the first or second limit detectors by the portion of the triggering element for activation of the first and second limit detectors results in counter-rotation of the container by the rotating means by activation of the respective limit detector; and vertical sensing means for sensing vertical movement of the animal, including an activating element which moves in response to vertical movement of the animal, and a vertical detecting element positioned for detection of movement of the activating element and providing an output therefrom such that vertical movement of the animal causes detection of the movement by the vertical detecting element and activation of the activating element.

17. The apparatus of claim 16, wherein the detecting element of the vertical sensing means comprises an optical sensor activated upon interruption of a light beam emanating therefrom.

18. The apparatus of claim 16, further comprising a pivotable counterbalanced arm for operable connection to the animal by the tethering means, and wherein the counterbalanced arm comprises the activating element of the vertical sensing means.

19. The apparatus of claim 16, further comprising:

means for analysis of the vertical movement of the animal operatively connected to the output of the vertical detecting element.

20. The apparatus of claim 19, wherein the analysis means comprises an input responsive to the output of the vertical detection element, and wherein the analysis means further comprises a timing means operatively connected to the input for associating time with the output of the vertical detection element, such that the means for analysis provides a time history of the vertical movement of the animal.

21. The apparatus of claim 19, wherein the analysis means comprises a strip chart recorder.

22. The apparatus of claim 19, wherein the analysis means comprises a data processor.

23. An apparatus for performing at least one biomedical test on a freely-moving animal, comprising:

a container for housing the animal;

means for rotating the container, the rotating means operably connected to the container;

means for sensing rotational movement of the animal, the sensing means including first and second activatable limit detectors having a primary sensing axis, the first and second limit detectors positioned such that the primary sensing axes of the limit detectors are at a predetermined relative position with respect to each other, the first and second limit detectors logically connected to the rotating means to cause clockwise and counterclockwise movement, respectively, of the rotating means upon activation thereof, and a moveable triggering element having at least a portion thereof for activation and deactivation of the first and second limit detectors;

means for supporting the sensing means above the animal, the support means connected to the sensing means;

means for tethering the animal to the sensing means, the tether means having first and second ends, the first end for connection to the animal, and the second end connected to the triggering element of the sensing means, the tethering means comprising first means for conducting fluid, such that rotational movement of the animal causes movement of the tether means which in turn causes movement of the triggering element of the sensing means, and upon activation of either the first or second limit detectors by the portion of the triggering element for activation of the first and second limit detectors results in counter-rotation of the container by the rotating means by activation of the respective limit detector; and a test device external the container, the test device comprising:

second means for conducting fluid including a first, a second and a third tube operatively connected to each other, the first tube operatively connected to the tethering means;

means for receiving fluid operatively connected to the second tube;

means for moving fluid operatively connected to the third tube; and a first and a second fluid control means, each of the first and second fluid control means having an open and a closed position, each of the first and second fluid control means operatively connected to the first, and second tube respectively such that when each of the first and second fluid control means is opened, fluid is free to flow through the respective tube, and when each of the first and second fluid control means is closed, fluid is prevented from flowing through the respective tube.

24. The apparatus of claim 23, further comprising:

sample collection control means for controlling fluid flow operatively connected to the means for moving fluid, and the first and second fluid control means.

25. The apparatus of claim 24, further comprising the sample collection control means operatively connected to the means for receiving fluid.

26. The apparatus of claim 24, wherein the sample collection control means comprises a personal computer.

27. The apparatus of claim 23, wherein each of the first and second fluid control means comprise a pinch valve.

28. The apparatus of claim 27, wherein the first and the second pinch valves jointly comprise a three-way pinch valve having a first and a second position, such that in the first position the first tube is closed and the second tube is open and in the second position the first tube is open and the second tube is closed.

29. The apparatus of claim 23, wherein the means for moving fluid comprises at least one syringe pump.

30. A method for performing automated micro fluid sampling, comprising the steps of:

providing the apparatus of claim 23, wherein the first, second, and third tubes are filled with solution, and wherein the first fluid control means is closed, and the second fluid control means is open;

pushing solution into the third tube using the means for moving fluid, thereby flushing the second tube with solution;

closing the second fluid control means and opening the first fluid control means;

withdrawing solution from the third tube with the means for moving fluid, thereby withdrawing a discreet amount of fluid from the animal, sufficient to fill the tethering means and the first tube with fluid and to fill the third tube with the desired fluid sample;

opening the second fluid control means and closing the first fluid control means;

pushing into the third tube with the means for moving fluid a volume of solution equal to the volume of the second tube, thereby forcing the fluid sample to the end of the second tube;

pushing from the means for moving fluid an amount of solution into the third tube equal to the volume of the fluid sample, thereby depositing the fluid sample into the means for receiving fluid;

closing the second fluid control means and opening the first fluid control means;

pushing from the fluid control means enough solution into the third tube to thereby force the fluid within the first tube and the tethering means back into the animal as well as an amount of solution equal to the volume of the fluid sample withdrawn.

31. The method for performing automated micro fluid sampling of claim 30, further providing a means for supplying solution, and providing a fourth tube operatively connecting the means for supplying solution and the means for moving fluid, such that the means for providing the solution is in communication with the means for moving fluid; and providing a third and a fourth fluid control means each having a closed and an open position, operatively connected to the third and the fourth tube respectively, such that when the third or fourth fluid control means is in the closed position, fluid is restricted from flowing in the respective tube, and when the third or fourth fluid control means is in the open position, fluid is free to flow in the respective tube, the invention comprising the steps of:
opening the fourth fluid control means, and closing the third fluid control means,
withdrawing solution with the means for moving fluid from the means for supplying solution, thereby refilling the means for moving fluid with solution;
closing the fourth fluid control means, and
opening the third fluid control means.

32. The method for performing automated micro fluid sampling of claim 30, further comprising, before the step of pushing solution into the third tube, the steps of:

providing sample collection control means for controlling fluid flow, the sample collection control means operatively connected to the means for moving fluid, and the first and second fluid control means; and activating the sample collection control means, such that subsequent steps are controlled by the sample collection control means.

33. The method for performing automated micro fluid sampling of claim 32, wherein the apparatus further comprises the sample collection control means operatively connected to the means for receiving fluid, further comprising after the step of pushing into the third tube with the means for moving fluid a volume of solution equal to the volume of the second tube, thereby forcing the fluid sample to the end of the second tube, the step;

positioning the means for receiving fluid so as to collect the fluid sample.

34. The apparatus of claim 23, wherein each of the first, second, and third tube is coated on its interior surface with an anticoagulant, and wherein the tethering means is coated on its interior surface with an anticoagulant.

35. An apparatus for performing at least one biomedical test on an animal, the apparatus comprising:

means for conducting fluid including a first, a second and a third tube operatively connected to each other, the first tube operatively connected to the animal;

means for receiving fluid operatively connected to the second tube;

means for moving fluid operatively connected to the third tube; and a first and a second fluid control means, each of the first and second fluid control means having an open and a closed position, each of the first and second fluid control means operatively connected to the first, and second tube respectively such that when each of the first and second fluid control means is opened, fluid is free to flow through the respective tube, and when each of the first and second fluid control means is closed, fluid is prevented from flowing through the respective tube.

36. The apparatus of claim 35, further comprising sample collection control means for controlling fluid flow operatively connected to the means for moving fluid and the first and the second fluid control means.

37. The apparatus of claim 36, wherein the sample collection control means is operatively connected to the means for receiving fluid.

38. The apparatus of claim 36, wherein the sample collection control means comprises a personal computer.

39. The apparatus of claim 35, wherein each of the first and the second fluid control means comprise a pinch valve.

40. The apparatus of claim 39, wherein the first and the second pinch valves jointly comprise a three-way pinch valve having a first and a second position, such that in the first position the first tube is closed and the second tube is open and in the second position the first tube is open and the second tube is closed.

41. The apparatus of claim 35, wherein the means for moving fluid comprises at least one syringe pump.

42. A method for performing automated micro fluid sampling, comprising the steps of:

providing the apparatus of claim 35, wherein the first, second, and third tubes are filled with solution, and wherein the first fluid control means is closed, and the second fluid control means is open;

pushing solution into the third tube using the means for moving fluid, thereby flushing the second tube with solution;

closing the second fluid control means and opening the first fluid control means;

withdrawing solution from the third tube with the means for moving fluid, thereby withdrawing a discreet amount of fluid from the animal, sufficient to fill the tethering means and the first tube with fluid and to fill the third tube with the desired fluid sample;

opening the second fluid control means and closing the first fluid control means;

pushing into the third tube with the means for moving fluid a volume of solution equal to the volume of the second tube, thereby forcing the fluid sample to the end of the second tube;

pushing from the means for moving fluid an amount of solution into the third tube equal to the volume of the fluid sample, thereby depositing the fluid sample into the means for receiving fluid;

closing the second fluid control means and opening the first fluid control means;

pushing from the fluid control means enough solution into the third tube to thereby force the fluid within the first tube and the tethering means back into the animal as well as an amount of solution equal to the volume of the fluid sample withdrawn.

43. The method for performing automated micro fluid sampling of claim 42, further providing means for supplying solution, and providing a fourth tube operatively connecting the means for supplying solution and the means for moving fluid, such that the means for providing the solution is in communication with the means for moving fluid; and providing a third and a fourth fluid control means each having a closed and an open position, operatively connected to the third and the fourth tube respectively, such that when the third or fourth fluid control means is in the closed position, fluid is restricted from flowing in the respective tube, and when the third or fourth fluid control means is in the open position, fluid is free to flow in the respective tube, the invention comprising the steps of:

opening the fourth fluid control means, and closing the third fluid control means, withdrawing solution with the means for moving fluid from the means for supplying solution, thereby refilling the means for moving fluid with solution;

closing the fourth fluid control means, and opening the third fluid control means.

44. The method for performing automated micro fluid sampling of claim 42, further comprising, before the step of pushing solution into the third tube, the steps of:

providing sample collection control means for controlling fluid flow, the sample collection control means operatively connected to the means for moving fluid, and the first and second fluid control means; and activating the sample collection control means, such that subsequent steps are controlled by the sample collection control means.

45. The method for performing automated micro fluid sampling of claim 44, wherein the apparatus further comprises the sample collection control means operatively connected to the means for receiving fluid, further comprising after the step of pushing into the third tube with the means for moving fluid a volume of solution equal to the volume of the second tube, thereby forcing the fluid sample to the end of the second tube, the step;

positioning the means for receiving fluid so as to collect the fluid sample.

46. The apparatus of claim 35, wherein each of the first, second, and third tube is coated on its interior surface with an anticoagulant.

* * * * *